United States Patent
Bermudez-Humaran et al.

(10) Patent No.: US 11,103,564 B2
(45) Date of Patent: *Aug. 31, 2021

(54) COMPOSITIONS FOR THE INHIBITION OF GIARDIA LAMBLIA

(71) Applicants: INSTITUT NATIONAL DE LA RECHERCHE AGRONOMIQUE, Paris (FR); MUSEUM NATIONAL D'HISTOIRE NATURELLE, Paris (FR); ECOLE NATIONALE VETERINAIRE D'ALFORT, Maison Alfort (FR)

(72) Inventors: Luis G. Bermudez-Humaran, Jouy en Josas (FR); Thibault Allain, Gentilly (FR); Isabelle Florent, Paris (FR); Philippe Langella, Velizy (FR); Philippe Grellier, Choisy-le-roi (FR); Marie-Agnes Travers, Marennes (FR); Bruno Polack, Paris (FR)

(73) Assignees: INSTITUT NATIONAL DE LA RECHERCHE AGRONOMIQUE, Paris (FR); MUSEUM NATIONAL D'HISTOIRE NATURELLE, Paris (FR); ECOLE NATIONALE VETERINAIRE D'ALFORT, Maison Alfort (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/445,569

(22) Filed: Jun. 19, 2019

(65) Prior Publication Data
US 2019/0323860 A1 Oct. 24, 2019

Related U.S. Application Data

(63) Continuation of application No. 15/501,587, filed as application No. PCT/EP2015/068334 on Aug. 10, 2015, now Pat. No. 10,328,132.

(30) Foreign Application Priority Data

Aug. 8, 2014 (EP) .................................. 14306265

(51) Int. Cl.
| | |
|---|---|
| *A61K 38/50* | (2006.01) |
| *C12N 9/80* | (2006.01) |
| *A61K 38/00* | (2006.01) |
| *A61K 38/16* | (2006.01) |
| *A61K 38/46* | (2006.01) |
| *A61K 35/741* | (2015.01) |
| *A61K 35/744* | (2015.01) |
| *A23L 33/135* | (2016.01) |
| *G01D 5/24* | (2006.01) |
| *H03K 17/955* | (2006.01) |

(52) U.S. Cl.
CPC ............ *A61K 38/50* (2013.01); *A23L 33/135* (2016.08); *A61K 35/741* (2013.01); *A61K 35/744* (2013.01); *A61K 38/00* (2013.01); *A61K 38/164* (2013.01); *A61K 38/46* (2013.01); *C12N 9/80* (2013.01); *C12Y 305/01024* (2013.01); *G01D 5/24* (2013.01); *H03K 17/955* (2013.01); *A23V 2002/00* (2013.01); *A23Y 2220/03* (2013.01); *A23Y 2220/37* (2013.01); *A23Y 2220/43* (2013.01); *H03K 2217/96075* (2013.01); *H03K 2217/960745* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 6,428,329 B2 | 8/2002 | Orui et al. | |
| 6,905,679 B1 | 6/2005 | Schiffrin | |
| 7,608,700 B2 | 10/2009 | Klaenhammer | |
| 10,328,132 B2 * | 6/2019 | Bermudez-Humaran | ................... A61K 38/00 |

FOREIGN PATENT DOCUMENTS

| | | |
|---|---|---|
| KR | 20090126757 A | 12/2009 |
| WO | 03/084989 A2 | 10/2003 |
| WO | 2004/076657 A2 | 9/2004 |

OTHER PUBLICATIONS

Houghten et al. (Vaccines, 1986, Edited by Fred Brown: Cold Spring Harbor Laboratory) (Year: 1986).*
Witkowski et al ( Biochemistry 38:11643-11650, 1999) (Year: 1999).*
Seffernick et al., (J. Bacteriol. 183(8): 2405-2410, 2001) (Year: 2001).*
UniProt Accession No. F4AEI5 (Year: 2011).*

(Continued)

*Primary Examiner* — Padmavathi Baskar
(74) *Attorney, Agent, or Firm* — Arrigo, Lee, Guttman & Mouta-Bellum LLP

(57) ABSTRACT

The present invention relates to a composition exhibiting a bile-salt hydrolase activity for its use for the treatment or the prevention of giardiasis, said composition comprising a bile-salt hydrolase (BSH)enzyme, a bacterium able to secrete a BSH, a recombinant host cell able to secrete a BSH, or a combination thereof. The present invention also relates to the use of a composition exhibiting a BSH activity for the treatment or the prevention of giardiasis, and to a pharmaceutical composition or a food composition comprising, as an active principle, a BSH, a lactic acid bacterium able to secrete a BSH, or a recombinant host cell able to secrete a BSH.

23 Claims, 14 Drawing Sheets

Figure 1A:
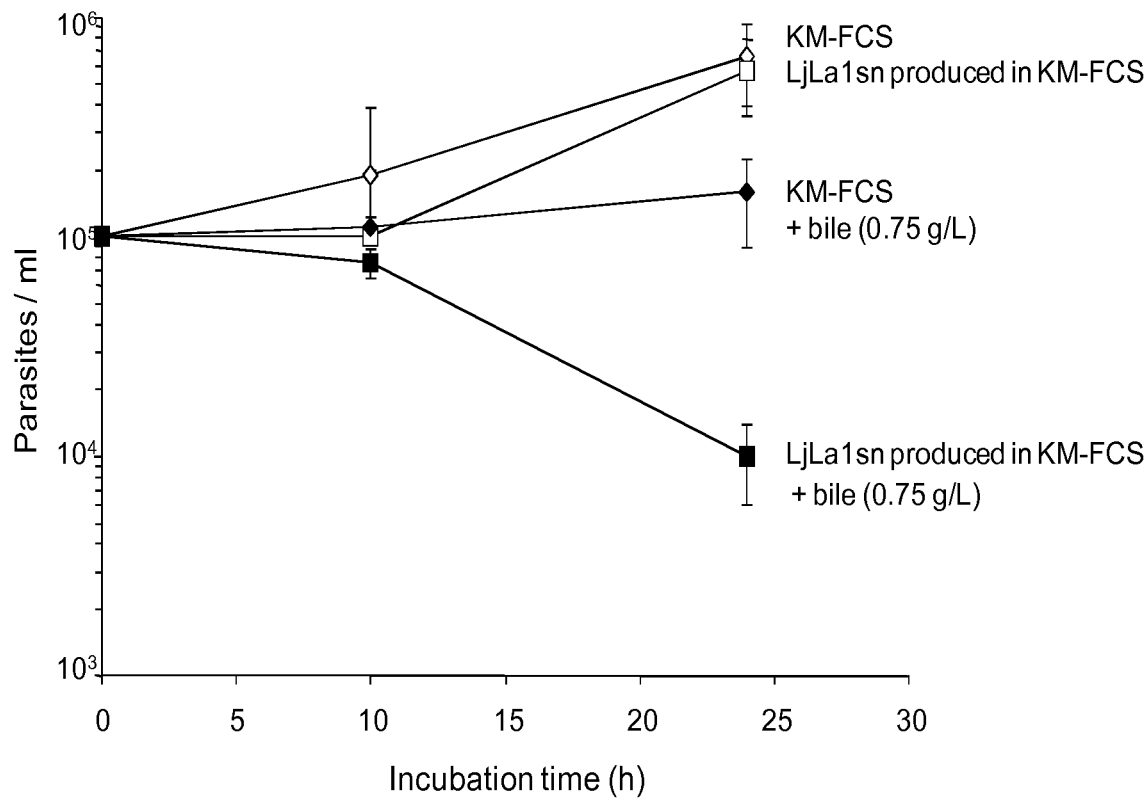

Specification includes a Sequence Listing.

(56) References Cited

OTHER PUBLICATIONS

Proc. Natl. Acad. Sci. U.S.A. 101:2512-2517(2004) (Year: 2004).*
Halliday, CEW, et al., "Characterization of Bile Salt Uptake by Giardia lamblia," International Journal for Parasitology, vol. 25, No. 9, pp. 1089-1097 (1995).
Humen, Martin A., et al., "Lactobacillus johnsonii La1 Antagonizes Giardia intestinalis In Vivo," Infection and Immunity, vol. 73, No. 2, p. 1265-69 (2005).
Pridmore, R. David, et al., "The genome sequence of the probiotic intestinal bacterium Lactobacillus johnsonii NCC 533," PNAS, vol. 101, No. 8, pp. 2512-2517 (2004).
Feng et al., (Infection and Immunity, 64(1):363-365, 1996).
Chapter 29 of "Vaccines" [Plotkin, S.A. et al. (eds) published by W. B. Saunders company (Philadelphia) in 1988.
The dictionary of Immunology, Herbert et al eds, Adademic Press, one page 1995.
Syed et al., Giardia intestinalis Current Opinion in Infectious Diseases 2003, 16:453-460.
International Search Report of PCT/EP2015/068334, dated Oct. 14, 2015.

* cited by examiner d- KM + Sup *LjLA1* + bile

SEQUENCE LISTING

```
<160> NUMBER OF SEQ ID NOS: 11

<210> SEQ ID NO 1
<211> LENGTH: 326
<212> TYPE: PRT
<213> ORGANISM: Lactobacillus johnsonii BSH-12

<400> SEQUENCE: 1

Met Cys Thr Ser Ile Val Tyr Ser Ser Asn Asn His His Tyr Phe Gly
1               5                   10                  15

Arg Asn Leu Asp Leu Glu Ile Ser Phe Gly Glu His Pro Val Ile Thr
            20                  25                  30

Pro Arg Asn Tyr Glu Phe Gln Tyr Arg Lys Leu Pro Ser Lys Lys Ala
        35                  40                  45

Lys Tyr Ala Met Val Gly Met Ala Ile Val Glu Asn Asn Tyr Pro Leu
    50                  55                  60

Tyr Phe Asp Ala Ala Asn Glu Glu Gly Leu Gly Ile Ala Gly Leu Asn
65                  70                  75                  80

Phe Asp Gly Pro Cys His Tyr Phe Pro Glu Asn Ala Glu Lys Asn Asn
                85                  90                  95

Val Thr Pro Phe Glu Leu Ile Pro Tyr Leu Leu Ser Gln Cys Thr Thr
            100                 105                 110

Val Ala Glu Val Lys Asp Ala Leu Lys Asp Val Ser Leu Val Asn Ile
        115                 120                 125

Asn Phe Ser Glu Lys Leu Pro Leu Ser Pro Leu His Trp Leu Met Ala
    130                 135                 140

Asp Lys Thr Gly Glu Ser Ile Val Val Glu Ser Thr Leu Ser Gly Leu
145                 150                 155                 160

His Val Tyr Asp Asn Pro Val His Val Leu Thr Asn Asn Pro Glu Phe
                165                 170                 175

Pro Gly Gln Leu Arg Asn Leu Ala Asn Tyr Ser Asn Ile Ala Pro Ala
            180                 185                 190

Gln Pro Lys Asn Thr Leu Val Pro Gly Val Asp Leu Asn Leu Tyr Ser
        195                 200                 205

Arg Gly Leu Gly Thr His Phe Leu Pro Gly Gly Met Asp Ser Ala Ser
    210                 215                 220

Arg Phe Val Lys Ile Ala Phe Val Arg Ala His Ser Pro Gln Gly Asn
225                 230                 235                 240

Asn Glu Leu Ser Ser Val Thr Asn Tyr Phe His Ile Leu His Ser Val
                245                 250                 255

Glu Gln Pro Lys Gly Thr Asp Glu Val Gly Pro Asn Ser Tyr Glu Tyr
            260                 265                 270

Thr Ile Tyr Ser Asp Gly Thr Asn Leu Glu Thr Gly Thr Phe Tyr Tyr
        275                 280                 285

Thr Asn Tyr Glu Asn Asn Gln Ile Asn Ala Ile Glu Leu Asn Lys Glu
    290                 295                 300
```

Asn Leu Asn Gly Asp Glu Leu Thr Asp Tyr Lys Leu Ile Glu Lys Gln
305                 310                 315                 320

Thr Ile Asn Tyr Gln Asn
            325

<210> SEQ ID NO 2
<211> LENGTH: 325
<212> TYPE: PRT
<213> ORGANISM: Lactobacillus johnsonii BSH-47

<400> SEQUENCE: 2

Met Cys Thr Ser Ile Leu Tyr Ser Pro Lys Asp Asn Tyr Phe Gly Arg
1               5                   10                  15

Asn Leu Asp Tyr Glu Ile Ala Tyr Gly Gln Lys Val Val Ile Thr Pro
            20                  25                  30

Arg Asn Tyr Gln Leu Asn Tyr Arg His Leu Pro Thr Gln Asp Thr His
        35                  40                  45

Tyr Ala Met Ile Gly Val Ser Val Ala Asn Asp Tyr Pro Leu Tyr
    50                  55                  60

Cys Asp Ala Ile Asn Glu Lys Gly Leu Gly Ile Ala Gly Leu Asn Phe
65                  70                  75                  80

Thr Gly Pro Gly Lys Tyr Phe Ser Val Asp Glu Ser Lys Lys Asn Val
                85                  90                  95

Thr Ser Phe Glu Leu Ile Pro Tyr Leu Leu Ser Asn Cys Glu Thr Ile
            100                 105                 110

Glu Asp Val Lys Lys Leu Leu Ser Glu Thr Asn Ile Thr Asp Glu Ser
        115                 120                 125

Phe Ser Lys Asp Leu Pro Val Thr Thr Leu His Trp Leu Met Gly Asp
130                 135                 140

Lys Ser Gly Lys Ser Ile Val Ile Glu Ser Thr Glu Thr Gly Leu His
145                 150                 155                 160

Val Tyr Asp Asn Pro Val Asn Thr Leu Thr Asn Asn Pro Val Phe Pro
                165                 170                 175

Ala Gln Val Glu Thr Leu Ala Asn Phe Ala Ser Val Ser Pro Ala Gln
            180                 185                 190

Pro Lys Asn Thr Leu Val Pro Asn Ala Asp Ile Asn Leu Tyr Ser Arg
        195                 200                 205

Gly Leu Gly Thr His His Leu Pro Gly Gly Thr Asp Ser Asn Ser Arg
    210                 215                 220

Phe Ile Lys Ala Ser Phe Val Leu Ala His Ser Pro Lys Gly Asn Asp
225                 230                 235                 240

Glu Val Glu Asn Val Thr Asn Phe Phe His Val Leu His Ser Val Glu
                245                 250                 255

Gln Ala Lys Gly Thr Asp Glu Val Glu Asp Asn Val Phe Glu Phe Thr
            260                 265                 270

Met Tyr Ser Asp Cys Met Asn Leu Asp Lys Gly Ile Leu Tyr Phe Thr
        275                 280                 285

Thr Tyr Asp Asn Asn Gln Ile Asn Ala Val Asp Met Asn Asn Glu Asp
    290                 295                 300

Leu Gly Thr Ser Asp Leu Ile Thr Tyr Glu Leu Phe Lys Asp Gln Ala
305                 310                 315                 320

Ile Lys Phe Glu Asn
            325

```
<210> SEQ ID NO 3
<211> LENGTH: 316
<212> TYPE: PRT
<213> ORGANISM: Lactobacillus johnsonii BSH-56

<400> SEQUENCE: 3

Met Cys Thr Gly Leu Arg Phe Thr Asp Asp Gln Gly Asn Leu Tyr Phe
1               5                   10                  15

Gly Arg Asn Leu Asp Val Gly Gln Asp Tyr Gly Glu Gly Val Ile Ile
            20                  25                  30

Thr Pro Arg Asn Tyr Pro Leu Pro Tyr Lys Phe Leu Asp Asn Thr Thr
        35                  40                  45

Thr Lys Lys Ala Val Ile Gly Met Gly Ile Val Val Asp Gly Tyr Pro
    50                  55                  60

Ser Tyr Phe Asp Cys Tyr Asn Glu Asp Gly Leu Gly Ile Ala Gly Leu
65                  70                  75                  80

Asn Phe Pro His Phe Ala Lys Phe Ser Asp Gly Pro Ile Asp Gly Lys
                85                  90                  95

Ile Asn Leu Ala Ser Tyr Glu Ile Met Leu Trp Val Thr Gln Asn Phe
            100                 105                 110

Thr His Val Ser Glu Val Lys Glu Ala Leu Lys Asn Val Asn Leu Val
        115                 120                 125

Asn Glu Ala Ile Asn Thr Ser Phe Ala Val Ala Pro Leu His Trp Ile
130                 135                 140

Ile Ser Asp Ser Asp Glu Ala Ile Ile Val Glu Val Ser Lys Gln Tyr
145                 150                 155                 160

Gly Met Lys Val Phe Asp Lys Val Gly Val Leu Thr Asn Ser Pro
                165                 170                 175

Asp Phe Asn Trp His Leu Thr Asn Leu Gly Asn Tyr Thr Gly Leu Asn
            180                 185                 190

Pro His Asp Ala Thr Ala Gln Ser Trp Asn Gly Gln Lys Val Ala Pro
        195                 200                 205

Trp Gly Val Gly Thr Gly Ser Leu Gly Leu Pro Gly Asp Ser Ile Pro
    210                 215                 220

Ala Asp Arg Phe Val Lys Ala Ala Tyr Leu Asn Val Asn Tyr Pro Thr
225                 230                 235                 240

Ala Lys Gly Glu Lys Ala Asn Val Ala Lys Phe Phe Asn Ile Leu Lys
                245                 250                 255

Ser Val Ala Met Ile Lys Gly Ser Val Val Asn Asp Gln Gly Lys Asp
            260                 265                 270

Glu Tyr Thr Val Tyr Thr Ala Cys Tyr Ser Ser Gly Ser Lys Thr Tyr
        275                 280                 285

Tyr Cys Asn Phe Glu Asp Phe Glu Leu Lys Thr Tyr Lys Leu Asp
    290                 295                 300

Asp His Thr Met Asn Ser Thr Ser Leu Val Thr Tyr
305                 310                 315

<210> SEQ ID NO 4
<211> LENGTH: 325
<212> TYPE: PRT
<213> ORGANISM: Lactobacillus gasseri BSH-A

<400> SEQUENCE: 4

Met Cys Thr Ser Ile Leu Tyr Ser Pro Lys Asp His Tyr Phe Gly Arg
1               5                   10                  15

Asn Leu Asp Tyr Glu Ile Ala Tyr Gly Gln Lys Val Val Ile Thr Pro
```

```
            20                  25                  30
Arg Asn Tyr Glu Phe Glu Phe Thr Asp Leu Pro Val Glu Lys Ser His
         35                  40                  45
Tyr Ala Met Ile Gly Val Ala Ala Val Ala Asp Asn Thr Pro Leu Tyr
 50                  55                  60
Cys Asp Ala Ile Asn Glu Lys Gly Leu Gly Val Ala Gly Leu Ser Phe
 65                  70                  75                  80
Ala Gly Gln Gly Lys Tyr Phe Pro Asn Ala Val Asn Lys Lys Asn Ile
                 85                  90                  95
Ala Ser Phe Glu Phe Ile Ser Tyr Leu Leu Ala Thr Tyr Glu Thr Val
            100                 105                 110
Asp Gln Val Lys Glu Ser Leu Thr Asn Ala Asn Ile Ser Asn Val Ser
            115                 120                 125
Phe Ala Lys Asn Thr Pro Ala Ser Glu Leu His Trp Leu Val Gly Asp
            130                 135                 140
Lys Thr Gly Lys Ser Ile Val Val Glu Ser Asp Glu Lys Gly Leu His
145                 150                 155                 160
Val Tyr Asn Asn Pro Val Asn Ala Leu Thr Asn Ala Pro Leu Phe Pro
                165                 170                 175
Glu Gln Leu Thr Asn Leu Val Asn Phe Ala Ser Val Val Pro Gly Glu
            180                 185                 190
Pro Asp Asn Asn Phe Leu Pro Gly Val Asn Leu Lys Leu Tyr Ser Arg
            195                 200                 205
Ser Leu Gly Thr His His Leu Pro Gly Gly Met Asp Ser Glu Ser Arg
            210                 215                 220
Phe Val Lys Val Cys Phe Ala Leu Asn His Ala Pro Lys Asp Ser Asp
225                 230                 235                 240
Glu Val Glu Asn Val Thr Asn Phe Phe His Ile Leu Glu Ser Val Glu
                245                 250                 255
Gln Ala Lys Gly Met Asp Gln Val Gly Pro Asn Ser Phe Glu Tyr Thr
            260                 265                 270
Met Tyr Thr Ser Cys Met Asn Leu Glu Lys Gly Ile Leu Tyr Phe Asn
            275                 280                 285
Cys Tyr Asp Asp Ser Arg Ile Ser Ala Val Asp Met Asn Lys Glu Asp
            290                 295                 300
Leu Asp Ser Ser Asp Leu Val Val Tyr Asp Leu Phe Lys Lys Gln Asp
305                 310                 315                 320
Ile Ser Phe Ile Asn
            325

<210> SEQ ID NO 5
<211> LENGTH: 325
<212> TYPE: PRT
<213> ORGANISM: Lactobacillus gasseri BSH-B

<400> SEQUENCE: 5

Met Cys Thr Ser Ile Leu Tyr Ser Pro Lys Asp His Tyr Phe Gly Arg
 1                5                  10                  15

Asn Leu Asp Tyr Glu Ile Ala Tyr Gly Gln Lys Val Val Ile Thr Pro
             20                  25                  30

Lys Asn Tyr Glu Phe Glu Phe Thr Asp Leu Pro Ala Glu Lys Ser His
             35                  40                  45

Tyr Ala Met Ile Gly Val Ala Ala Val Ala Asp Asn Thr Pro Leu Tyr
 50                  55                  60
```

```
Cys Asp Ala Ile Asn Glu Lys Gly Leu Gly Val Ala Gly Leu Ser Phe
 65                  70                  75                  80

Ala Gly Gln Gly Lys Tyr Phe Pro Asn Ala Ala Asp Lys Lys Asn Ile
                 85                  90                  95

Ala Ser Phe Glu Phe Ile Ser Tyr Leu Leu Ala Thr Tyr Glu Thr Val
            100                 105                 110

Asp Gln Val Lys Glu Ser Leu Thr Asn Ala Asn Ile Ser Asn Val Ser
        115                 120                 125

Phe Ala Lys Asn Thr Pro Ala Ser Glu Leu His Trp Leu Val Gly Asp
130                 135                 140

Lys Thr Gly Lys Ser Ile Val Val Glu Ser Asp Glu Lys Gly Leu His
145                 150                 155                 160

Val Tyr Asn Asn Pro Val Asn Ala Leu Thr Asn Ala Pro Leu Phe Pro
                165                 170                 175

Glu Gln Leu Thr Asn Leu Ala Asn Tyr Ala Ser Val Val Pro Gly Glu
            180                 185                 190

Pro Asp Asn Asn Phe Leu Pro Gly Val Asn Leu Lys Leu Tyr Ser Arg
        195                 200                 205

Ser Leu Gly Thr His His Leu Pro Gly Gly Met Asp Ser Glu Ser Arg
210                 215                 220

Phe Val Lys Val Cys Phe Ala Leu Asn His Ala Pro Lys Asp Ser Asp
225                 230                 235                 240

Glu Val Glu Asn Val Thr Asn Phe Phe His Ile Leu Glu Ser Val Glu
                245                 250                 255

Gln Ala Lys Gly Met Asp Gln Ile Gly Pro Asn Ser Phe Glu Tyr Thr
            260                 265                 270

Met Tyr Thr Ser Cys Met Asn Leu Glu Lys Gly Ile Leu Tyr Phe Asn
        275                 280                 285

Cys Tyr Asp Asp Ser Arg Ile Ser Ala Val Asp Met Asn Lys Glu Asp
290                 295                 300

Leu Asp Ser Ser Asp Leu Val Tyr Asp Leu Phe Lys Lys Gln Asp
305                 310                 315                 320

Ile Ser Phe Ile Asn
            325

<210> SEQ ID NO 6
<211> LENGTH: 325
<212> TYPE: PRT
<213> ORGANISM: Lactobacillus johnsonii DPC6026 (F4AEI5)

<400> SEQUENCE: 6

Met Cys Thr Ser Ile Leu Tyr Ser Pro Lys Asp Asn Tyr Phe Gly Arg
 1                5                  10                  15

Asn Leu Asp Tyr Glu Ile Ala Tyr Gly Gln Lys Val Val Ile Thr Pro
                 20                  25                  30

Arg Asn Tyr Gln Leu Asp Tyr Arg His Leu Pro Thr Gln Asp Thr His
             35                  40                  45

Tyr Ala Met Ile Gly Val Ser Val Val Ala Asn Asp Tyr Pro Leu Tyr
         50                  55                  60

Cys Asp Ala Ile Asn Glu Lys Gly Leu Gly Ile Ala Gly Leu Asn Phe
 65                  70                  75                  80

Thr Gly Pro Gly Lys Tyr Phe Ala Val Asp Glu Ser Lys Lys Asn Val
                 85                  90                  95

Thr Ser Phe Glu Leu Ile Pro Tyr Leu Leu Ser Ser Cys Glu Thr Ile
            100                 105                 110
```

```
Glu Asp Val Lys Lys Leu Leu Ser Glu Thr Asn Ile Thr Asp Glu Ser
            115                 120                 125

Phe Ser Lys Asp Leu Pro Val Thr Thr Leu His Trp Leu Met Gly Asp
130                 135                 140

Lys Ser Gly Lys Ser Ile Val Ile Glu Ser Thr Glu Thr Gly Leu His
145                 150                 155                 160

Val Tyr Asp Asn Pro Val Asn Thr Leu Thr Asn Asn Pro Val Phe Pro
                165                 170                 175

Ala Gln Val Glu Thr Leu Ala Asn Phe Ala Ser Val Ser Pro Ala Gln
            180                 185                 190

Pro Lys Asn Thr Leu Val Pro Asn Ala Asp Ile Asn Leu Tyr Ser Arg
        195                 200                 205

Gly Leu Gly Thr His His Leu Pro Gly Gly Thr Asp Ser Asn Ser Arg
    210                 215                 220

Phe Ile Lys Ala Ser Phe Val Leu Ala His Ser Pro Lys Gly Asn Asp
225                 230                 235                 240

Glu Val Glu Asn Val Thr Asn Phe Phe His Ile Leu His Ser Val Glu
                245                 250                 255

Gln Ala Lys Gly Thr Asp Glu Val Glu Asp Asn Val Phe Glu Phe Thr
            260                 265                 270

Met Tyr Ser Asp Cys Met Asn Leu Asp Lys Gly Ile Leu Tyr Phe Thr
        275                 280                 285

Thr Tyr Asp Asn Asn Gln Ile Asn Ala Val Asp Met Asn Asn Glu Asp
    290                 295                 300

Leu Asp Thr Ser Asp Leu Ile Thr Tyr Glu Leu Phe Lys Asp Gln Ala
305                 310                 315                 320

Ile Lys Phe Glu Asn
                325

<210> SEQ ID NO 7
<211> LENGTH: 326
<212> TYPE: PRT
<213> ORGANISM: Lactobacillus johnsonii DPC6026 (F4ACA3)

<400> SEQUENCE: 7

Met Cys Thr Ser Ile Val Tyr Ser Ser Asn Asn His His Tyr Phe Gly
1               5                   10                  15

Arg Asn Leu Asp Leu Glu Ile Ser Phe Gly Glu His Pro Val Ile Thr
            20                  25                  30

Pro Arg Asn Tyr Glu Phe Gln Tyr Arg Lys Leu Pro Ser Lys Lys Ala
        35                  40                  45

Lys Tyr Ala Met Val Gly Met Ala Ile Val Glu Asn Asn Tyr Pro Leu
    50                  55                  60

Tyr Phe Asp Ala Ala Asn Glu Glu Gly Leu Gly Ile Ala Gly Leu Asn
65                  70                  75                  80

Phe Asp Gly Pro Cys His Tyr Phe Pro Glu Asn Ala Glu Lys Asn Asn
                85                  90                  95

Val Thr Pro Phe Glu Leu Ile Pro Tyr Leu Leu Ser Gln Cys Thr Thr
            100                 105                 110

Val Ala Glu Val Lys Asp Ala Leu Lys Asp Val Ser Leu Val Asn Ile
        115                 120                 125

Asn Phe Ser Glu Lys Leu Pro Leu Ser Pro Leu His Trp Leu Met Ala
    130                 135                 140

Asp Lys Thr Gly Glu Ser Ile Val Val Glu Ser Thr Leu Ser Gly Leu
```

```
            145                 150                 155                 160
        His Val Tyr Asp Asn Pro Val His Val Leu Thr Asn Asn Pro Glu Phe
                    165                 170                 175

Pro Gly Gln Leu Arg Asn Leu Ala Asn Tyr Ser Asn Ile Ala Pro Ala
                    180                 185                 190

Gln Pro Lys Asn Thr Leu Val Pro Gly Val Asp Leu Asn Leu Tyr Ser
                    195                 200                 205

Arg Gly Leu Gly Thr His Phe Leu Pro Gly Gly Met Asp Ser Ala Ser
            210                 215                 220

Arg Phe Val Lys Val Ala Phe Val Arg Ala His Ser Pro Gln Gly Asn
        225                 230                 235                 240

Asn Glu Leu Ser Ser Val Thr Asn Tyr Phe His Ile Leu His Ser Val
                    245                 250                 255

Glu Gln Pro Lys Gly Thr Asp Glu Val Gly Pro Asn Ser Tyr Glu Tyr
                    260                 265                 270

Thr Ile Tyr Ser Asp Gly Thr Asn Leu Glu Thr Gly Thr Phe Tyr Tyr
                    275                 280                 285

Thr Asn Tyr Glu Asn Asn Gln Ile Asn Ala Ile Glu Leu Asn Lys Glu
                    290                 295                 300

Asn Leu Asn Gly Asp Glu Leu Ile Asp Tyr Lys Leu Ile Glu Lys Gln
        305                 310                 315                 320

Thr Ile Asn Tyr Gln Asn
                    325

<210> SEQ ID NO 8
<211> LENGTH: 316
<212> TYPE: PRT
<213> ORGANISM: Lactobacillus johnsonii DPC6026 (F4ADE7)

<400> SEQUENCE: 8

Met Cys Thr Gly Leu Arg Phe Thr Asp Asp Gln Gly Asn Leu Tyr Phe
        1               5                   10                  15

Gly Arg Asn Leu Asp Val Gly Gln Asp Tyr Gly Glu Gly Val Ile Ile
                    20                  25                  30

Thr Pro Arg Asn Tyr Pro Leu Pro Tyr Lys Phe Leu Asp Asn Thr Thr
                    35                  40                  45

Thr Lys Lys Ala Val Ile Gly Met Gly Ile Val Val Asp Gly Tyr Pro
            50                  55                  60

Ser Tyr Phe Asp Cys Tyr Asn Glu Asp Gly Leu Gly Ile Ala Gly Leu
        65                  70                  75                  80

Asn Phe Pro His Phe Ala Lys Phe Ser Asp Gly Pro Ile Asp Gly Lys
                    85                  90                  95

Ile Asn Leu Ala Ser Tyr Glu Ile Met Leu Trp Val Thr Gln Asn Phe
                    100                 105                 110

Thr His Val Ser Glu Val Lys Glu Ala Leu Lys Asn Val Asn Leu Val
                    115                 120                 125

Asn Glu Ala Ile Asn Thr Ser Phe Ala Val Ala Pro Leu His Trp Ile
                    130                 135                 140

Ile Ser Asp Ser Asp Glu Ala Ile Ile Val Glu Val Ser Lys Gln Tyr
        145                 150                 155                 160

Gly Met Lys Val Phe Asp Asp Lys Val Gly Val Leu Thr Asn Ser Pro
                    165                 170                 175

Asp Phe Asn Trp His Leu Thr Asn Leu Gly Asn Tyr Thr Gly Leu Asn
                    180                 185                 190
```

```
Pro His Asp Ala Thr Ala Gln Ser Trp Asn Gly Gln Lys Val Ala Pro
            195                 200                 205

Trp Gly Val Gly Thr Gly Ser Leu Gly Leu Pro Gly Asp Ser Ile Pro
        210                 215                 220

Ala Asp Arg Phe Val Lys Ala Ala Tyr Leu Asn Val Asn Tyr Pro Thr
225                 230                 235                 240

Ala Lys Gly Glu Lys Ala Asn Val Ala Lys Phe Asn Ile Leu Lys
                245                 250                 255

Ser Val Ala Met Ile Lys Gly Ser Val Val Asn Asp Gln Lys Asp
            260                 265                 270

Glu Tyr Thr Val Tyr Thr Ala Cys Tyr Ser Ser Gly Ser Lys Thr Tyr
        275                 280                 285

Tyr Cys Asn Phe Glu Asp Asp Phe Glu Leu Lys Thr Tyr Lys Leu Asp
290                 295                 300

Asp His Thr Met Asn Ser Thr Ser Leu Val Thr Tyr
305                 310                 315

<210> SEQ ID NO 9
<211> LENGTH: 981
<212> TYPE: DNA
<213> ORGANISM: Lactobacillus johnsonii La1 BSH-12

<400> SEQUENCE: 9
ctaattttga taattaattg tttgcttttc aatcaacttg taatctgtta actcatcacc      60
atttaagttt tctttattta attcaatggc gttaatttga ttattttcat aattggtata     120
ataaaacgtg cctgtctcca agttagttcc atcagagtaa attgtgtact cataagaatt     180
tggtccgact tcatctgttc cctttggctg ttcaaccgaa tgtaaaatat ggaataatt      240 tgttacacta cttaattcat tatttccttg aggggaatgt gcccgaacaa aagctatttt     300
cacaaaacga ctggccgaat ccattcctcc tggcaaaaaa tgagtccta  acccgcgact     360 atataaatta aggtcaacac ctggaacaag agtatttta  ggctgtgcag gtgctatatt     420
actataatta gctaagttac gtaactggcc tggaaattca ggattattgg ttaaaacatg     480
aactggatta tcataaacgt gtaatccact taaagtcgat tctacaacga tcgactcacc     540
agtcttatca gccattaacc agtgaagtgg agaaagtggt agttttttctg aaaagtttat    600 atttactaag ctaacatctt tcaatgcatc ttttacttca gcaaccgtag tacattgact     660
tagcaaataa ggaattaatt caaatggtgt aacattattt ttctccgcat ttctggaaa     720 ataatgacac ggaccatcaa aattaaggcc agcaattcct agcccttctt catttgctgc     780
atcaaaatat agtggataat tatttttctac aatcgccatc ccaaccatgg catattttgc     840 cttttttactt ggtaatttac gatattgaaa ctcataattc cttggtgtaa ttacaggatg     900
ttcaccaaaa gaaatttcca agtctagatt tcggccaaaa taatgatgat tatttgaact     960
ataaacaatt gaggtacaca t                                              981

<210> SEQ ID NO 10
<211> LENGTH: 978
<212> TYPE: DNA
<213> ORGANISM: Lactobacillus johnsonii La1 BSH-47

<400> SEQUENCE: 10
atgtgtacat caattttata tagtccaaaa gataattatt ttggtagaaa tttagattat      60
gaaattgcct atggtcagaa agtggtaatt actcctagaa attatcaact taattaccga    120
catttaccaa cacaagatac tcattatgca atgatcggtg tttcagtagt cgccaatgac    180
```

| | |
|---|---|
| tatccattat attgtgatgc tatcaatgaa aagggactag ggatagccgg attaaatttc | 240 |
| actggtcctg gtaaatattt ttctgtagat gaaagtaaaa agaatgttac ttcttttgaa | 300 |
| ctgatcccat atttactaag taattgcgaa actatcgaag atgtaaagaa attattatct | 360 |
| gaaactaata ttactgatga agtttctct aaagatttac cagttactac tcttcattgg | 420 |
| ttaatgggtg ataaaagtgg taagagtata gtcattgaat caacagaaac tggcttacac | 480 |
| gtttatgaca acccagttaa tactttaaca aataatcctg tctttccagc tcaagttgaa | 540 |
| accttggcta actttgcttc agtttctcca gctcaaccta agaataccct tgtacctaat | 600 |
| gcagatatta atctgtatag ccgtggatta gggacccatc atttaccagg cggaacagat | 660 |
| tcaaattctc gctttattaa ggcatctttt gtattagctc attctccaaa aggtaatgat | 720 |
| gaagtcgaaa atgtaactaa tttcttccat gtcttacatt cagttgaaca agcaaagggt | 780 |
| acagatgaag ttgaagataa tgtatttgaa tttaccatgt attcagactg tatgaatttg | 840 |
| gataaaggaa ttttatactt tactacttac gataataacc aaattaatgc tgtggatatg | 900 |
| aataatgaag atttaggtac ttctgacttg atcacttatg aattatttaa ggatcaagcc | 960 |
| attaaatttg aaaattaa | 978 |

<210> SEQ ID NO 11
<211> LENGTH: 951
<212> TYPE: DNA
<213> ORGANISM: Lactobacillus johnsonii La1 BSH-56

<400> SEQUENCE: 11

| | |
|---|---|
| ctagtaagtc acaagactgg ttgaattcat cgtgtgatca tctagtttat aggtctttaa | 60 |
| ttcaaaatca tcttcaaaat tacagtagta agtcttgctt ccagaagagt agcatgcagt | 120 |
| ataaacagta tattcgtcct tgccttgatc gttgactaca ctgcctttga tcatggcaac | 180 |
| agactttaag atgttaaaga atttagcgac gtttgctttt tcacctttag cagttggata | 240 |
| gtttacgttt aagtaagcag ctttaacaaa acgatcggct ggaatactgt caccgggcag | 300 |
| acctaagcta ccagttccta cgccccaagg agcaactttt tgcccgttcc agctttgggc | 360 |
| tgtagcgtca tgtgggttta aaccggtgta gttaccaagg ttagtaaggt gccagttaaa | 420 |
| gtcagggcta ttagttaaaa cgccaacttt gtcatcaaag actttcattc catattgttt | 480 |
| tgaaacctca acaataatgg cttcgtcact atcactaatg atccagtgaa gagggcaac | 540 |
| cgcaaatgat gtgttaatag cttcattcac taagttaaca ttctttaaag cttcctttac | 600 |
| ttcactaaca tgagtaaagt tttgagtaac ccagagcata atttcgtaag aagctaagtt | 660 |
| gattttaccg tcaataggac catcactaaa tttagcaaaa tgtgggaagt ttaaacctgc | 720 |
| aatacctaat ccatcttcgt tatagcagtc aaagtatgat ggatagccat caaccacaat | 780 |
| tcccattcca ataacagcct ttttagtagt ggtgttatct aagaacttat atggaagagg | 840 |
| ataattacgc ggcgtaataa taacgccttc gccataatcc tgtccaacat ctagattacg | 900 |
| gccaaagtat aaatttcctt gatcatctgt gaatcttaaa ccagtacaca t | 951 |

COMPOSITIONS FOR THE INHIBITION OF *GIARDIA LAMBLIA*

The present invention relates to a composition exhibiting a bile-salt hydrolase activity for its use for the treatment or the prevention of giardiasis, said composition comprising a bile-salt hydrolase (BSH) enzyme, a bacterium able to secrete a BSH, a recombinant host cell able to secrete a BSH, or a combination thereof. The present invention also relates to the use of a composition exhibiting a BSH activity for the treatment or the prevention of giardiasis, and to a pharmaceutical composition or a food composition comprising, as an active principle, a BSH, a bacterium able to secrete a BSH, or a recombinant host cell able to secrete a BSH.

*Giardia lamblia* is a parasitic protozoan responsible for giardiasis, a disease characterized by acute or chronic intestinal malabsorption, diarrhea, weight loss, dehydration and abdominal pain in humans and a variety of animals. It is one of the most common intestinal parasites in the world. Giardiasis has high veterinary impact and high impact on public health, is responsible for important human morbidity, especially causing nutritional deficiencies in children in developing countries (Ali and Hill, 2003). Developed countries are also concerned by giardiasis and outbreaks have been associated with drinking water contamination resulting from runoff of contaminated soils by rain falls, agricultural practices and sewage treatment plant dysfunctions (Mons et al., 2009).

*G. lamblia* enters vertebrates when cysts are ingested with food, water or fomites contaminated by feces from infected hosts. Cysts remain infective for months in environmental waters. They are highly resistant to chlorinated disinfectants used in drinking water treatments and infectious doses are low (10 to 100 cysts). After ingestion, infective forms excyst, releasing trophozoites that establish infections in the upper small intestine (duodenum) where they interact with the intestinal barrier. Duodenum is a very specific environment where food from the stomach, bile from the gall bladder and digestive enzymes from the pancreas pour in. There, *G. lamblia* divides by binary fission and eventually exits the host with the feces once trophozoites have re-formed cysts. The drug of choice for treating giardiasis remains metronidazole, a 5-nitroimidazole, which is reduced into toxic compounds by the parasite enzyme pyruvate: ferredoxin oxido-reductase. Side effects of drug treatment are reported and metronidazole resistance appears in vitro and in clinical settings (up to 20% of environmental strains were reported as resistant) (Uperoft and Uperoft, 2001).

How *Giardia* pathology is produced is still unclear but it is probably multifactorial (Farthing et al., 1997). Pathophysiologies observed comprise damages of the host mucosal surface by microvillus and crypt atrophy, decreased epithelial permeability and impairment of the activity of digestive enzymes. These changes may be due as much to factors of the host as to those of the parasite.

It is now widely recognized that intestine microbiota plays a role in the protection of the host against gut colonization by pathogens (Travers et al., 2011). Different mechanisms may be responsible for the protective effects: competition for pathogen receptor sites, barrier for pathogen access, production of antimicrobial compounds, competition for nutritional substrates and enhancement of the innate and adaptive host immune responses (Tancrede et al., 1992). Nutritional strategies are based on an increase of the components of the gut microbiota that are associated with the protective activity (Brassard D. and Schiffrin E J., 1997). Colonization of the intestine by *G. lamblia* strongly depends on the gut microbiota (Singer and Nash, 2000). Evidences strongly suggest the involvement of the bacterium *Enterococcus faecium* in the host immune response against *G. lamblia* (Benyacoub et al., 2005). Extracellular factors of *L. johnsonii* La1 block the in vitro growth of *G. lamblia* in G1 phase indicating that bacteria may directly affect parasite development (Perez et al., 2001). It was shown that the probiotic bacteria *Lactobacillus johnsonii* La1 antagonizes *G. lamblia* establishment in rodent model (Humen et al., 2005).

The increasing numbers of outbreaks of giardiasis due to drinking water contamination, the side effects of available anti-*Giardia* drugs as well as, the increasing emergence of resistance to these drugs, render giardiasis a worrying subject, and there is a real need for alternative therapeutic strategies.

The present invention now provides compositions exhibiting a bile-salt hydrolase (BSH) activity as effective inhibitors for *Giardia lamblia*, for the prevention or the treatment of giardiasis. The inventors have indeed shown that parasite growth inhibition is mediated by secreted bacteria bile-salt hydrolase activity(ies) that produce(s) deconjugated bile salts from bile present in the culture medium, and that, unlike normal conjugated bile salts which are the main components of the bile, deconjugated bile salts are found toxic for *Giardia*.

Anti-*Giardia* activity was studied in vivo and in vitro for *L. johnsonii* La1 (LjL1) (Perez et al. 2001, Humen et al. 2005). The genomes of *L. johnsonii* La1 and *G. lamblia* were sequenced (Pridmore et al. 2004, Morrison et al. 2007). Halliday et al (1995) disclose that *G. lamblia* internalizes conjugated bile salts, however this document does not mention a role for unconjugated bile salts. Shukla et al. (2011, 2012, 2013) describe that the administration of *Lactobacillus rhamnosus* lessens the severity of giardiasis. U.S. Pat. No. 6,905,679 discloses a method for the treatment of a disorder associated with the colonization of gut by *Giardia intestinalis* comprising the administration of *Lactobacillus acidophilus* La10 bacteria (CNCM reference number I-2332), of *Bifidobacterium bifidum* (I-2333) or of *Bifidobacterium infantis* (I-2334). The inhibitory effect of lactic acid bacteria is possibly attributed to particular organic acids secreted by said lactic acid bacteria.

However, none of these documents disclose the role of bile-salt hydrolase activity, in the presence of bile salts, for the inhibition of *Giardia lamblia*.

A composition according to the present invention represents a new therapeutic strategy against *Giardia lamblia*, based on the natural catalytic activity of bile-salt hydrolases, in order to prevent or treat giardiasis. A composition according to the invention furthermore represents a public health interest by providing a means to counteract the emergence of drug resistant *Giardia* strains.

The invention will become more fully understood from the detailed description given herein and from the accompanying drawings, which are given by way of illustration only and do not limit the intended scope of the invention.

The present invention first relates to a composition exhibiting a bile-salt hydrolase activity for the treatment or the prevention of giardiasis.

The term "bile-salt hydrolase activity" or "BSH activity" refers to the ability of a composition according to the invention to hydrolyse conjugated bile-salts to generate deconjugated bile salts, and glycine or taurine. BSH cleave the peptide linkage of bile acids, which results in removal of the amino acid group from the steroid core and in the production of deconjugated, or unconjugated, bile acids, which precipitate at low pH.

The expression "treatment or prevention of giardiasis" refers to the treatment or the prevention of disorders associated with the presence in the gut of *Giardia lamblia* or of *Giardia intestinalis*, and in particular disorders associated with the infestation and/or colonization of the gut by said parasites.

Conjugated bile salts, or bile acids, are glycocholic acid (GCA), taurocholic acid (TCA), glycodeoxycholic acid (GDCA), taurodeoxycholic acid (TDCA), glycochenodeoxycholic acid (GCDCA) and taurochenodeoxycholic acid (TCDCA). Unconjugated bile-salts, also called deconjugated bile salts are: cholic acid (CA), deoxycholic acid (DCA) and chenodeoxycholic acid (CDCA).

BSH activity is assessed by the detection the products generated by the enzymatic reaction, in particular the detection:
of glycine and/or taurine, liberated from conjugated bile salts,
of cholic acid (CA), deoxycholic acid (DCA) and/or chenodeoxycholic acid (CDCA)
by classical detection methods well known by a person skilled in the art of enzymology, including, without restriction, chromatography, mass-spectrometry, proteomic analysis, spectrophotometry, fluorometry, colorimetry or chemiluminescence, and any method such as described in the present specification. In a particular embodiment, CA, DCA and/or CDCA are detected by mass spectrometry analysis (LC/ESI-MS analysis) of bile components, and proteomic analysis.

A specific method for detection of BSH activity includes a method such as described in the present specification, using mass spectrometry analysis (LC/ESI-MS analysis) and proteomic analysis of bile components. It may also be detected, in bacteria, by a method comprising the growth of said bacteria in an adapted broth, the streaking of bacteria onto medium supplemented, or not, with 0.2% (wt/vol) glycodeoxycholic acid and anaerobic incubation for 48 h. The white precipitates around colonies and the clearing of the medium are indicative of BSH activity.

Therefore, the present invention relates to a composition exhibiting a bile-salt hydrolase activity for the treatment or the prevention of giardiasis, said composition comprising at least one of the following elements, or a combination thereof:
A bile-salt hydrolase (BSH) enzyme,
A bacterium able to secrete at least one BSH, with the exception of the bacterial strains *Lactobacillus johnsonii* La1 (public reference NCC533, CNCM I-1225), *Lactobacillus acidophilus* La10 (NCC90, CNCM I-2332), *Bifidobacterium bifidum* (NCC189, CNCM I-2333) and *Bifidobacterium infantis* (NCC200, CNCM I-2334),
A recombinant host cell able to secrete at least one BSH.

The present invention also relates to a composition exhibiting a bile-salt hydrolase activity for the treatment or the prevention of giardiasis, said composition comprising at least one of the following elements, or a combination thereof:
A bile-salt hydrolase (BSH) enzyme,
A bacterium able to secrete at least one BSH, with the exception of the bacterial strains *Lactobacillus johnsonii* La1 (public reference NCC533, CNCM I-1225), *Lactobacillus acidophilus* (NCC90, CNCM I-2332), *Bifidobacterium bifidum* (NCC189, CNCM I-2333) and *Bifidobacterium infantis* (NCC200, CNCM I-2334),
A recombinant host cell able to secrete at least one BSH, wherein said BSH activity is determined by the detection of the presence of glycine or taurine, liberated from conjugated bile salts, or by the detection of the presence of cholic acid (CA), deoxycholic acid (DCA), and/or chenodeoxycholic acid (CDCA).

The BSH activity of a BSH enzyme is expressed as enzymatic units (U) when tested using a taurodeoxycholic and/or a glycodeoxycholic substrate. An example of this determination is described in Example 13 of the present patent application. The level of the activity of a BSH, in a composition according to the invention, can be expressed by reference to the activity of commercial *C. perfringens* BSH, and possibly using a test for said activity as described in the *C. perfringens* manufacturer's notice.

In a particular embodiment, the present invention relates to a composition exhibiting a BSH activity for use for the treatment or prevention of giardiasis, wherein said BSH activity is comprised between 0.0001 U and 100 U, between 0.001 U and 10 U, between 0.01 U and 1 U, between 0.1 U and 0.5 U.

In a first particular embodiment, the present invention relates to a composition exhibiting a bile-salt hydrolase activity for the treatment or the prevention of giardiasis, wherein the bile-salt hydrolase activity is associated with the presence of at least one bile-salt hydrolase (BSH) enzyme.

In another particular embodiment, the present invention relates to a composition exhibiting a BSH activity for use for the treatment or prevention of giardiasis, wherein said composition comprises a BSH enzyme, or is a able to secrete at least one BSH enzyme, wherein the concentration of BSH present in said composition is comprised between 0.01 µg/ml and 10 mg/ml, between 0.1 µg/ml and 1 mg/ml, between 0.5 µg/ml and 200 µg/ml, between, between 1 µg/ml and 100 µg/ml, between 1 µg/ml and 50 µg/ml or between 5 µg/ml and 20 µg/ml. In a more particular embodiment, a composition according to the invention exhibits a bile-salt hydrolase activity associated with the presence of at least one bile-salt hydrolase (BSH) enzyme, said enzyme being chosen among prokaryotic BSH, or BSH synthesized by bacteria. In a more particular embodiment, a composition according to the invention exhibits a bile-salt hydrolase activity associated with the presence of at least one bile-salt hydrolase (BSH) enzyme synthetized by a lactic acid bacterium.

A lactic acid bacterium is defined as gram positive bacteria sharing common metabolic and physiological characters, wherein lactic acid is produced as a major metabolic end product of carbohydrate fermentation. The group of lactic acid bacteria includes in particular *Lactobacillus*, *Lactococcus* and *Bifidobacterium*. In a more particular embodiment, a composition according to the invention exhibits a bile-salt hydrolase activity associated with the presence of at least one bile-salt hydrolase (BSH) enzyme which amino acid sequence comprises an amino acid sequence having at least 80% identity, at leat 85%, at least 90%, at least 95%, at least 98% or at least 99% identity with, or which is a natural variant of, an amino acid sequence chosen in the group consisting of:
*Lactobacillus johnsonii* La1 BSH-12 (LJ 1412) (SEQ ID No1, UniProtKB entry number Q74IV4
*Lactobacillus johnsonii* La1 BSH-47 (LJ 1147) (SEQ ID No2, UniProtKB entry number Q74JG0)
*Lactobacillus johnsonii* La1 BSH-56 (LJ 0056) (SEQ ID No3, UniProtKB entry number Q74LX7)
*Lactobacillus gasseri* (ATCC reference: 33323) BSH-A (SEQ ID No4, UniProtKB entry number B9V405)

*Lactobacillus gasseri* BSH-B (SEQ ID No5, UniProtKB entry number Q9AHJ7)
*Lactobacillus johnsonii* DPC 6026 (SEQ ID No6, UniProtKB entry number F4AEI5),
*Lactobacillus johnsonii* DPC 6026 (SEQ ID No7, UniProtKB entry number F4ACA3),
*Lactobacillus johnsonii* DPC 6026 (SEQ ID No8, UniProtKB entry number F4ADE7).

Any BSH enzyme suitable in a composition according to the present invention is easily found by a man skilled in the art, and may be chosen, in particular, among the following:
*Lactobacillus johnsonii* DPC 6026 BSH, UniProtKB entry number F4AEI5,
*Lactobacillus johnsonii* DPC 6026 BSH, UniProtKB entry number F4ACA3,
*Lactobacillus johnsonii* DPC 6026 BSH, UniProtKB entry number F4ADE7,
*Lactobacillus johnsonii* pf01 BSH, UniProtKB entry number F7SHH3, and
*Lactobacillus johnsonii* pf01 BSH, UniProtKB entry number F7SGA1.

The present invention comprises the presence of variants of BSH enzymes having at least 80%, at least 85%, preferably 90%, at least 90%, more preferably 95%, at least 95% and even more preferably 98%, at least 98% or at least 99% identity with a sequence chosen in the group consisting of SEQ ID No1 to SEQ ID No7. As used herein the term "identity" herein means that two amino acid sequences are identical (i.e. at the amino acid by amino acid) over the window of comparison. The term "percentage of sequence identity" is calculated by comparing two optimally aligned sequences over the window of comparison, determining the number of positions at which the identical amino acid residues occurs in both sequences to yield the number of matched positions, dividing the number of matched positions by the total number of positions in the window of comparison (i.e. the window size) and multiplying the result by 100 to yield the percentage of sequence identity. The percentage of sequence identity of an amino acid sequence can also be calculated using BLAST software with the default or user defined parameter. As applied to polypeptides, the term substantial identity means that two peptide sequences, when optimally aligned, share at least about 80% sequence identity, preferably at least 85% identity, preferably at least about 90% sequence identity, more preferably at least about 95% sequence identity, at least 98% sequence identity or more (e.g., 99% sequence identity). As used herein, a "derivative" or "sequence derived from", or "natural variant" refers to an amino acid sequence having at least 80% identity, preferably at least 85% identity, more preferably at least 90% identity and even more preferably at least 95% identity or more, such as at least 98% sequence identity or 99% identity with said reference amino acid sequence.

More particularly, the present invention refers to a composition exhibiting a bile-salt hydrolase activity associated with a BSH enzyme, for its use in the prevention of the treatment of giardiasis, wherein the amino acid sequence of said enzyme is chosen among the following:
*Lactobacillus johnsonii* La1 BSH-12 (SEQ ID No1),
*Lactobacillus johnsonii* La1 BSH-47 (SEQ ID No2),
*Lactobacillus johnsonii* La1 BSH-56 (SEQ ID No3),
*Lactobacillus gasseri* BSH-A (SEQ ID No4),
*Lactobacillus gasseri* BSH-B (SEQ ID No5),
*Lactobacillus johnsonii* DPC 6026 BSH (SEQ ID No6), UniProtKB entry number F4AEI5,
*Lactobacillus johnsonii* DPC 6026 BSH (SEQ ID No7), UniProtKB entry number F4ACA3,
*Lactobacillus johnsonii* DPC 6026 BSH (SEQ ID No8). UniProtKB entry number F4ADE7

In another particular embodiment, the invention relates to a composition exhibiting a bile-salt hydrolase activity for its use in the prevention of the treatment of giardiasis, wherein said composition comprises a lactic acid bacteria able to secrete a BSH, said lactic acid bacteria being chosen among: *Lactococcus, Lactobacillus*, with the exception of the bacterial strains *Lactobacillus johnsonii* La1 (NCC533, CNCM I-1225) and of *Lactobacillus acidophilus* (NCC90, CNCM I-2332), and *Bifidobacterium*, with the exception of the bacterial strains *Bifidobacterium bifidum* (NCC189, CNCM I-2333) and of *Bifidobacterium infantis* (NCC200, CNCM I-2334).

The term "lactic acid bacteria" refers to the presence of at least one micro-organism, wherein the micro-organism is preferably present of about 106 to 1012 cfu (colony forming unit). The microorganisms may be present as such or optionally after a step of purification from a culture medium. In another embodiment, a composition according to the invention comprises the supernatant of a culture medium of said microorganism, which may be concentrated by any method known by a man skilled in the art.

Therefore, the invention relates to a composition exhibiting a bile-salt hydrolase activity for its use in the prevention of the treatment of giardiasis, said composition comprising a *Lactobacillus*, with the exception of the bacterial strains *Lactobacillus johnsonii* La1 (NCC533, CNCM I-1225) and of *Lactobacillus acidophilus* (NCC90, CNCM I-2332).

The invention also relates to a composition exhibiting a bile-salt hydrolase activity for its use in the prevention of the treatment of giardiasis, said composition comprising a *Bifidobacterium*, with the exception of the bacterial strains *Bifidobacterium bifidum* (NCC189, CNCM I-2333) and of *Bifidobacterium infantis* (NCC200, CNCM I-2334).

In a more particular aspect, a composition according to the invention comprises a *Lactobacillus* chosen in the group consisting of:
*Lactobacillus johnsonii*, with the exception of the bacterial strains *Lactobacillus johnsonii* La1 (NCC533, CNCM I-1225)
*Lactobacillus gasseri*,
*Lactobacillus acidophilus*, with the exception of *Lactobacillus acidophilus* (NCC90, CNCM I-2332), and
*Lactobacillus reuteri*.

The following bacterial strains have shown a particular activity in a composition according to the invention, as shown in the "Examples" part of the specification.

In a particular embodiment, the invention relates to a composition exhibiting a bile-salt hydrolase activity for its use in the prevention of the treatment of giardiasis, said composition comprising a *lactobacillus* chosen in the group consisting of the bacterial strains referenced as:
*Lactobacillus johnsonii:*
Bacterial strain deposited at the CNCM, Institut Pasteur, Paris, under the number I-4885, on Aug. 7, 2014
Bacterial strain deposited under the reference CIP103614,
Bacterial strain deposited under the reference CIP 103786,
Bacterial strain deposited under the reference CIP 103620,
Bacterial strain deposited under the reference CIP103652,
Bacterial strain deposited under the reference CIP103653,
Bacterial strain deposited under the reference CIP103654,
Bacterial strain deposited under the reference CIP103781,
Bacterial strain deposited under the reference CIP103782,
*Lactobacillus gasseri:*
Bacterial strain deposited under the reference ATCC33353, Bacterial strain deposited at the CNCM, Institut Pasteur, Paris, under the number I-4884, on Aug. 7, 2014,
Bacterial strain deposited under the reference LMG11413, *Lactobacillus acidophilus*
Bacterial strain deposited under the reference ATCC700396.

In a particular embodiment, the present invention relates to a composition exhibiting a BSH activity for the prevention or the treatment of giardiasis, said composition comprising a lactic acid bacteria able to secrete a BSH, wherein said bacteria are present in an amount comprised between $10^6$ to $10^{12}$ cfu/g of bacteria.

In another particular embodiment, the present invention relates to a composition exhibiting a bile-salt hydrolase activity for its use in the prevention of the treatment of giardiasis, said composition comprising a host cell comprising a heterologous nucleic acid sequence encoding for at least one bile-salt hydrolase enzyme, said host cell being able to secrete said bile-salt hydrolase enzyme.

The term "host cell" refers to a living cell able to receive heterologous nucleic acid, and able to synthesize at least one protein encoded by said heterologous nucleic acid. In a preferred embodiment, said heterologous nucleic acid is an expression vector containing nucleic acid sequences able to encode a protein of interest and all necessary regulatory elements for the production of said protein in said host cell.

In a more particular embodiment, a composition according to the invention comprises a host cell comprising at least one nucleic acid sequence chosen among the following:
nucleotide sequence encoding for *L. johnsonii* La1 BSH-12 (SEQ ID No9), or a natural variant thereof, wherein said natural variant has a nucleotide sequence of at least 80%, at least 85%, at least 90%, at least 95%, at least 98%, or at least 99% identity with SEQ ID No9,
nucleotide sequence encoding for *L. johnsonii* La1 BSH-47 (SEQ ID No10), or a natural variant thereof, wherein said natural variant has a nucleotide sequence of at least 80%, at least 85%, at least 90%, at least 95%, at least 98%, or at least 99% identity with SEQ ID No10,
nucleotide sequence encoding for *L. johnsonii* La1 BSH-56 (SEQ ID No11), or a natural variant thereof, wherein said natural variant has a nucleotide sequence of at least 80%, at least 85%, at least 90%, at least 95%, at least 98%, or at least 99% identity with SEQ ID No11.

In another particular embodiment, the invention relates to a host cell for use in the treatment or the prevention of giardiasis, said host cell comprising at least one nucleic acid sequence, wherein said at least one nucleic acid sequence may be heterologous, chosen among the following:
nucleotide sequence encoding for *L. johnsonii* La1 BSH-12 (SEQ ID No9), or a natural variant thereof, wherein said natural variant has a nucleotide sequence of at least 80%, at least 85%, at least 90%, at least 95%, at least 98%, or at least 99% identity with SEQ ID No9,
nucleotide sequence encoding for *L. johnsonii* La1 BSH-47 (SEQ ID No10), or a natural variant thereof, wherein said natural variant has a nucleotide sequence of at least 80%, at least 85%, at least 90%, at least 95%, at least 98%, or at least 99% identity with SEQ ID No10,
nucleotide sequence encoding for *L. johnsonii* La1 BSH-56 (SEQ ID No11), or a natural variant thereof, wherein said natural variant has a nucleotide sequence of at least 80%, at least 85%, at least 90%, at least 95%, at least 98%, or at least 99% identity with SEQ ID No11.

Any BSH enzyme suitable in a composition according to the present invention can be selected by a man skilled in the art, and a nucleotide sequence encoding for said enzyme can be found in public databases, it may be chosen, in particular, among the following:
*Lactobacillus johnsonii* DPC 6026 BSH, UniProtKB entry number F4AEI5,
*Lactobacillus johnsonii* DPC 6026 BSH, UniProtKB entry number F4ACA3,
*Lactobacillus johnsonii* DPC 6026 BSH, UniProtKB entry number F4ADE7,
*Lactobacillus johnsonii* pf01 BSH, UniProtKB entry number F7SHH3,
*Lactobacillus johnsonii* pf01 BSH, UniProtKB entry number F7SGA1,
*Clostridium perfringens* BSH
*Lactobacillus acidophilus* BSH, bacterial strain referenced as ATCC700396.

In a more particular embodiment, a composition according to the present invention comprises a host cell comprising at least one nucleic acid sequence encoding for a BSH, said host cell being chosen in the group of lactic acid bacteria. More particularly, said lactic acid bacterium is chosen among lactobacilli and lactococci. In a particular embodiment of the invention, said lactic acid bacterium is *Lactococcus lactis*. In another particular embodiment of the invention, said lactic acid bacterium is a lactobacilli chosen among the group consisting of:
*Lactobacillus johnsonii*,
*Lactobacillus reuteri*, and
L *Lactobacillus gasseri*.

In another aspect, the present invention relates to the use of a composition exhibiting a bile-salt hydrolase activity for the treatment or the prevention of giardiasis, wherein said composition comprises:
A bile-salt hydrolase (BSH) enzyme,
A bacteria able to secrete at least one BSH, with the exception of the strain *Lactobacillus johnsonii* La1, *Lactobacillus acidophilus*, *Bifidobacterium bifidum* and *Bifidobacterium infantis*,
A recombinant host cell able to secrete at least one heterologous BSH, or
A combination thereof.

In a more particular embodiment, the present invention relates to the use of a composition exhibiting a bile-salt hydrolase activity wherein said composition comprises: a bile-salt hydrolase (BSH) enzyme, a bacteria able to secrete at least one BSH, with the exception of the strain *Lactobacillus johnsonii* La1, *Lactobacillus acidophilus*, *Bifidobacterium bifidum* and *Bifidobacterium infantis*, a recombinant host cell able to secrete at least one heterologous BSH, or a combination thereof for the treatment or the prevention of giardiasis, in human beings.

In another more particular embodiment, the present invention relates to the use of a composition exhibiting a bile-salt hydrolase activity wherein said composition comprises: a bile-salt hydrolase (BSH) enzyme, a bacteria able to secrete at least one BSH, with the exception of the strain *Lactobacillus johnsonii* La1, a recombinant host cell able to secrete at least one heterologous BSH, or a combination thereof for the treatment or the prevention of giardiasis in animals. Indeed, a composition according to the invention may be used for the treatment or the prevention of giardiasis in pigs and in cows, therefore, in a particular embodiment, a composition according to the invention is for use in the treatment or prevention of giardiasis in pigs or in cows.

In a further aspect, the present invention relates to a pharmaceutical composition comprising, as an active principle, a BSH, a lactic acid bacteria able to secrete at least a BSH, a host cell able to secrete a BSH, or a combination thereof, and a pharmaceutically acceptable carrier.

A pharmaceutical composition according to the invention comprises an effective amount of a BSH, a lactic acid bacteria able to secrete at least a BSH, a host cell able to secrete a BSH, or a combination thereof, and a pharmaceutically acceptable carrier, wherein said effective amount is defined as catalytic units (U), for BSH enzyme or recombinant BSH enzyme, or as a number of colony forming units (cfu), for living bacteria.

A pharmaceutical composition according to the invention is selected from an orally administrable composition, including, with no restriction, tablets, liquid bacterial suspension, dried oral supplement, wet oral supplement and tube feeding compositions.

Other pharmaceutical or nutritional preparations suitable for oral administration are hard or soft gelatin capsules made from gelatin and a plasticizer such as glycerol or sorbitol. Hard capsules may include the inventive compound in admixture with fillers such as lactose, binders such as starches, and/or lubricants such as talc or magnesium stearate, and if desired, stabilizers. In soft capsules, the inventive compound is preferably dissolved or suspended in a suitable liquid, such as fatty oil, paraffin oil or a liquid polyethylene glycol, to which a stabilizer can be added.

In a particular embodiment, a pharmaceutical composition according to the invention comprises an effective amount of a BSH enzyme and a pharmaceutically acceptable carrier for an administration to animals. In a more particular embodiment, a pharmaceutical composition from the invention comprises a BSH-12, a BSH-47 and/or a BSH-56 enzyme, and a carrier comprising a vehicle for oral administration of molecules, mixed with a cell culture buffer.

A person skilled in the art is able to choose an adapted vehicle, as an example, the SYRSPEND® can be cited, and to prepare and adapted mixture for its oral administration, for example by mixing said vehicle with a diluting solution and/or with a buffer. As an example, a a pharmaceutical composition according to the invention comprises an effective amount of BSH-12, a BSH-47 and/or a BSH-56 enzyme and a carrier comprising a mixture of SYRSPEND® NaHCO3 16.4%, DMEM (Dilbecco Modified Culture Medium).

Coated tablet cores can be provided with suitable coatings, which if appropriate are resistant to gastric juices, using, inter alia, concentrated sugar solutions which may contain gum arabic, talc, polyvinylpyrrolidone, polyethylene glycol and/or titanium dioxide, shellac solutions in suitable organic solvents or solvent mixtures or, for the preparation of coatings resistant to gastric juices, solutions of suitable cellulose preparations such as acetylcellulose phthalate or hydroxypropylmethylcellulose phthalate. Dyes or pigments can be added to the tablets or coated tablets, for example, to identify or indicate different doses of the active compound ingredient.

In a more particular embodiment, the present invention relates to a pharmaceutical composition comprising a BSH, a lactic acid bacterium able to secrete at least a BSH, a host cell able to secrete a BSH, or a combination thereof as an active principle, wherein said active principle is encapsulated.

In another particular embodiment, the present invention relates to a process for the preparation of a composition exhibiting a bile-salt hydrolase activity for the treatment or the prevention of giardiasis, said composition comprising a carrier and at least one of the following elements, or a combination thereof:

A bile-salt hydrolase (BSH) enzyme,

A bacterium able to secrete at least one BSH, with the exception of the bacterial strains *Lactobacillus johnsonii* La1 (public reference NCC533, CNCM I-1225), *Lactobacillus acidophilus* La10 (NCC90, CNCM I-2332), *Bifidobacterium bifidum* (NCC189, CNCM I-2333) and *Bifidobacterium infantis* (NCC200, CNCM I-2334), A recombinant host cell able to secrete at least one BSH.

In a more particular embodiment, the present invention relates to a process for the preparation of a composition exhibiting a bile-salt hydrolase activity for the treatment or the prevention of giardiasis, said composition comprising a pharmaceutically acceptable carrier and at least one of the following elements, or a combination thereof:

A bile-salt hydrolase (BSH) enzyme,

A bacterium able to secrete at least one BSH, with the exception of the bacterial strains *Lactobacillus johnsonii* La1 (public reference NCC533, CNCM I-1225), *Lactobacillus acidophilus* La10 (NCC90, CNCM I-2332), *Bifidobacterium bifidum* (NCC189, CNCM I-2333) and *Bifidobacterium infantis* (NCC200, CNCM I-2334), A recombinant host cell able to secrete at least one BSH.

In another more particular embodiment, the present invention relates to a process for the preparation of a composition exhibiting a bile-salt hydrolase activity for the treatment or the prevention of giardiasis, said composition comprising a carrier acceptable for a food composition or a dietary supplement and at least one of the following elements, or a combination thereof:

A bile-salt hydrolase (BSH) enzyme,

A bacterium able to secrete at least one BSH, with the exception of the bacterial strains *Lactobacillus johnsonii* La1 (public reference NCC533, CNCM I-1225), *Lactobacillus acidophilus* La10 (NCC90, CNCM I-2332), *Bifidobacterium bifidum* (NCC189, CNCM I-2333) and *Bifidobacterium infantis* (NCC200, CNCM I-2334), A recombinant host cell able to secrete at least one BSH.

A process according to the invention comprises at least a step of contacting said carrier with an effective amount of said enzyme and/or said bacterium and/or said host/cell, wherein said and a step of mixing said elements in order to prepare a composition suitable for its intended use.

The present invention also relates to a method for the prevention or for the treatment of giardiasis, said method comprising the administration, to a patient in need thereof, of a composition comprising at least one of the following elements, or a combination thereof:

A bile-salt hydrolase (BSH) enzyme,

A bacterium able to secrete at least one BSH, with the exception of the bacterial strains *Lactobacillus johnsonii* La1 (public reference NCC533, CNCM I-1225), *Lactobacillus acidophilus* (NCC90, CNCM I-2332), *Bifidobacterium bifidum* (NCC189, CNCM I-2333) and *Bifidobacterium infantis* (NCC200, CNCM I-2334), A recombinant host cell able to secrete at least one BSH, In a further aspect, the present invention relates to a food composition or a dietary supplement comprising, as an active principle, a BSH, a lactic acid bacterium able to secrete at least a BSH, a host cell able to secrete a BSH, or a combination thereof, and optionally a carrier.

A food composition or a dietary supplement according to the invention comprise an effective amount of a BSH, a lactic acid bacteria able to secrete at least a BSH, a host cell able to secrete a BSH, or a combination thereof, and a pharmaceutically acceptable carrier, wherein said effective amount is defined as catalytic units (U), for BSH enzyme or recombinant BSH enzyme, or as a number of colony forming units (cfu), for living bacteria.

A food composition or a dietary supplement according to the invention may be provided as a dry or a wet composition, and may be selected, with no restriction, among milk, yogurt, cheese, milk powder and pet food.

LEGENDS OF THE FIGURES

Figure 1B:
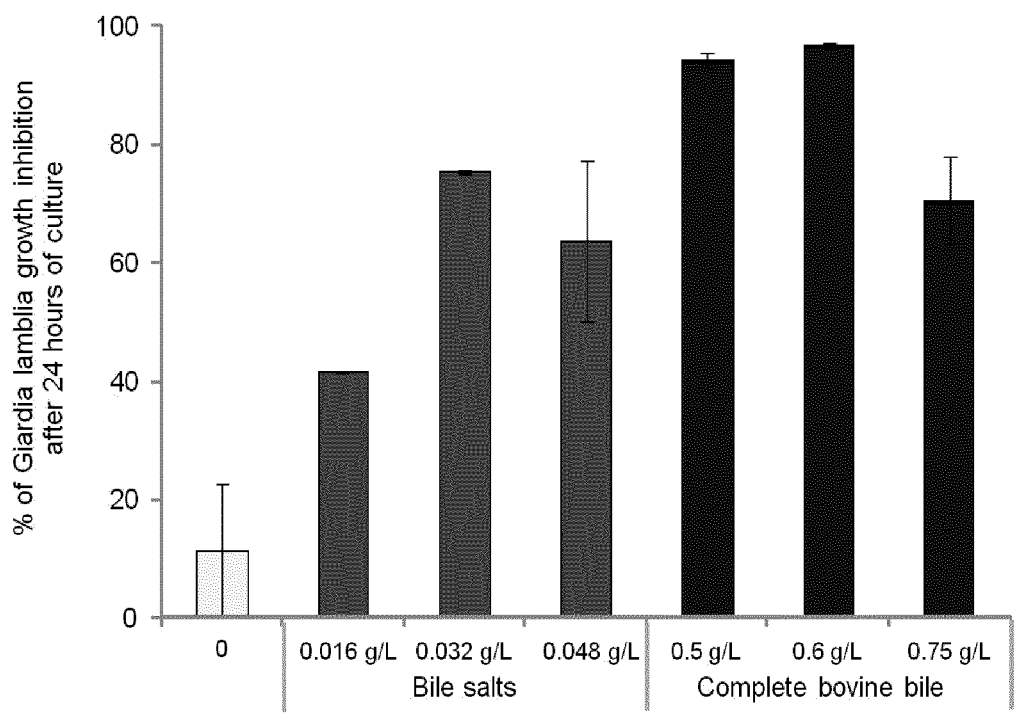

FIGS. 1A and 1B: inhibitory effect of LjLa1 supernatant on *G. lamblia*. FIG. 1A represents parasites concentration as a function of incubation time in the presence of KM-FCS with (filled symbols) or without (open symbols) bovine bile (0.75 g/L, final concentration), in presence (squares) or absence (diamonds) of bacterial supernatant (LjLa1sn). The parasite concentration was estimated by counting lived cells with a Malassez cell chamber, as indicated in example 1. N=2. FIG. 1B represents the percentage of *G. lamblia* growth inhibition after 24 h of culture is expressed as a function of bile salts concentration (grey histograms) or of complete bovine bile (black histograms, right part of the figure). *G. lamblia* trophozoites in KM-FCS were incubated for 24 h at 37° C. in anaerobic conditions with LjLA1sn and various concentrations of bile salts (0.016, 0.032, 0.048 g/L, final concentration) or complete bovine bile (0.5, 0.6, 0.75 g/L, final concentration). Growth inhibition values (%) were normalized according to control in lactic acid-acidified KM-FCS supplemented with similar concentrations of bovine bile or bile salts. Number of independent experiments=3.

Figure 2A:
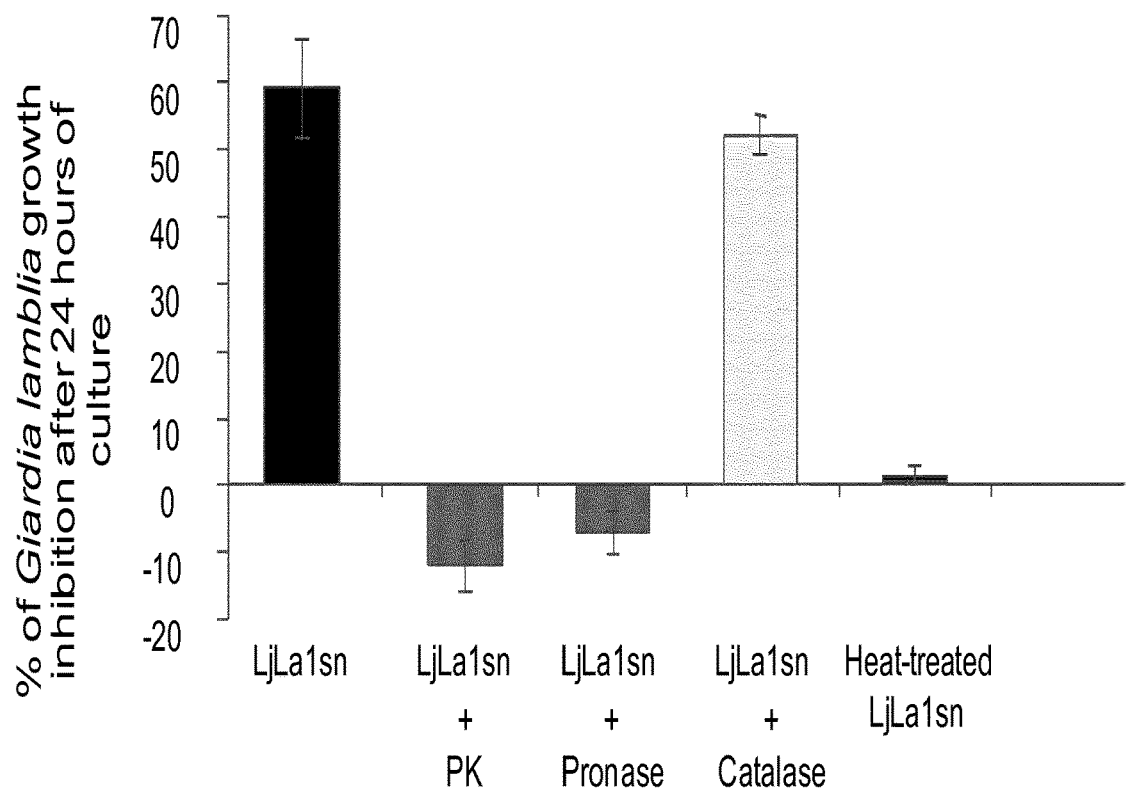
Figure 2B:
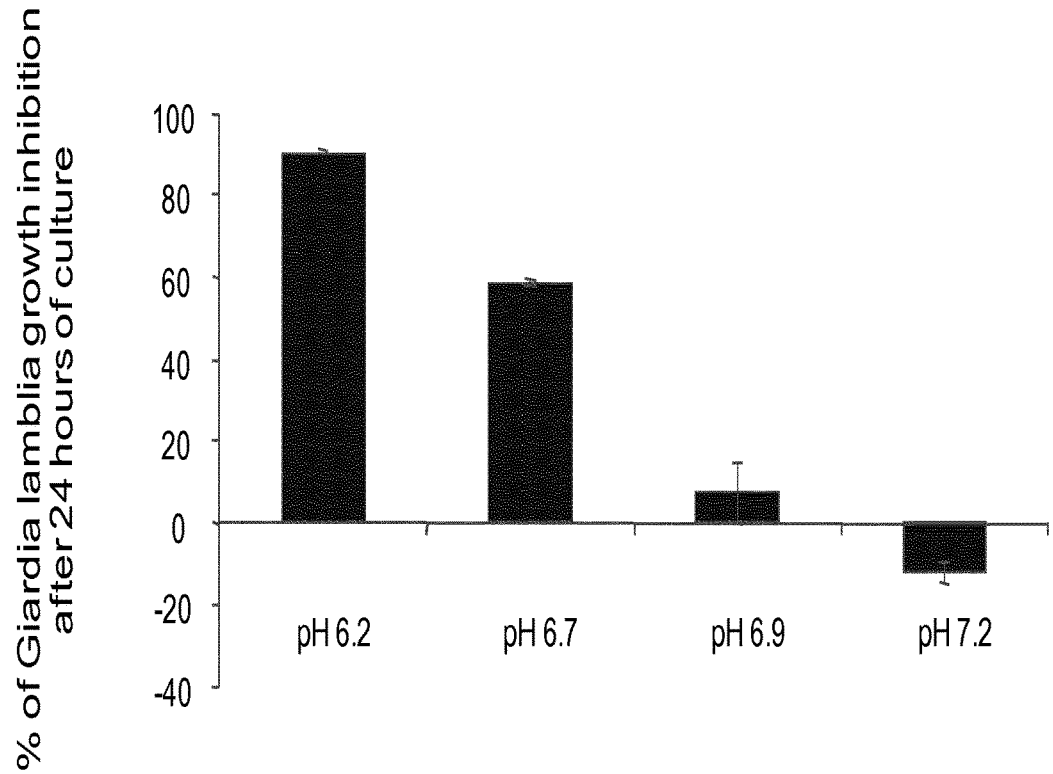
Figure 2C:
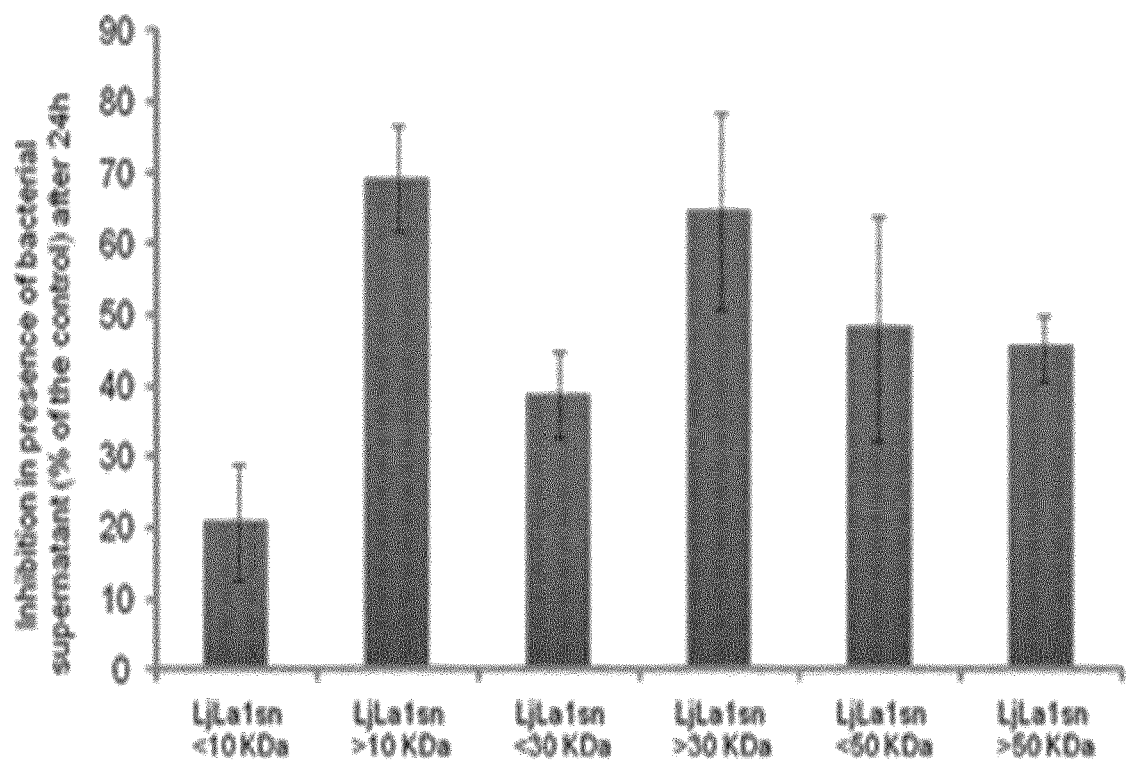

FIGS. 2A to 2C: percentage of *G. lamblia* growth inhibition after 24 h of culture. FIG. 2A represents the percentage of *G. lamblia* in the presence of (from left to right) LjLa1sn with no protease treatment, LjLa1sn with proteinase K, LjLa1sn with pronase; LjLa1sn with catalase or heated at 90° C. for 10 min before *G. lamblia* growth inhibition assay. Growth inhibition (%) was normalized according to matched control: lactic acid-adjusted MTYI medium incubated with protease-coupled beads or treated for 10 min at 90° C. Number of independent experiments=3. FIG. 2B represents the percentage of *G. lamblia* growth inhibition after 24 h of culture in varying pH. Supernatant from LjLa1 in MTYI medium was adjusted to pH 6.2, 6.7, 6.9 or 7.2 (histograms from left to right) before *Giardia* growth inhibition assays. Growth inhibition (%) was normalized according to control, i.e. lactic acid-adjusted MTYI subsequently raised to pH 6.2, 6.7, 6.9 or 7.2. Number of independent experiments=3. FIG. 2C represents the percentage of *G. lamblia* growth inhibition after 24 h of culture in supernatant from a culture of LjLa1 in KM-FCS medium filtrated through a 10 kDa, 30 kDa or 50 kDa MW cut-off membrane (from left to right). Acidified KM-FCS alone was processed similarly. Fractions above and under respective thresholds were assayed for *Giardia* growth inhibition in presence of bile (0.5 g/L). Inhibition values (%) were normalized according to KM-FCS controls. Number of independent experiments=3.

Figure 3A:
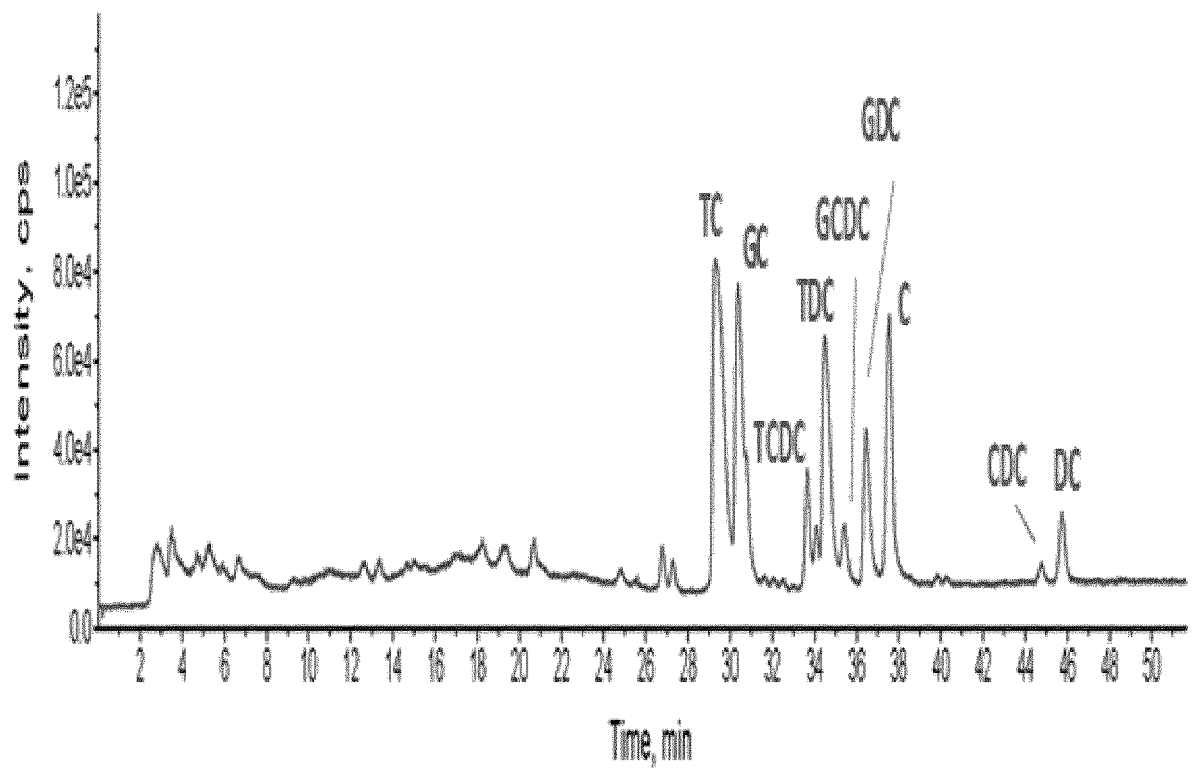
Figure 3B:
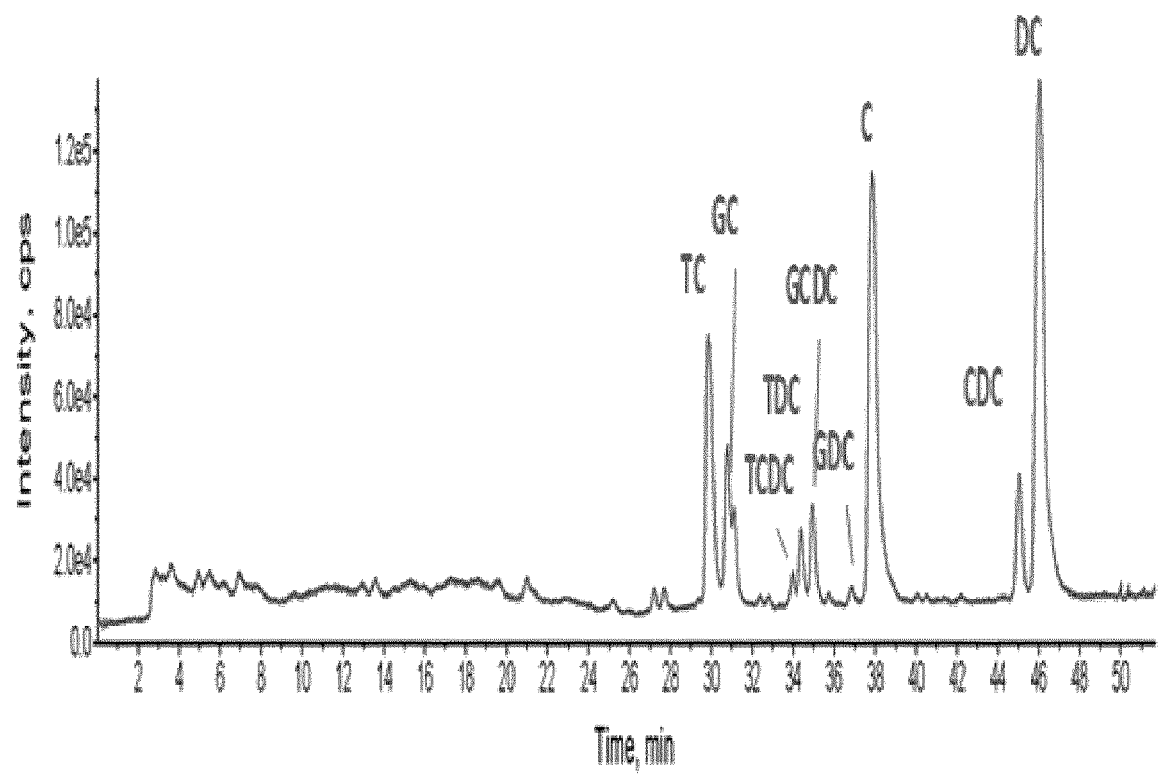
Figure 3C:
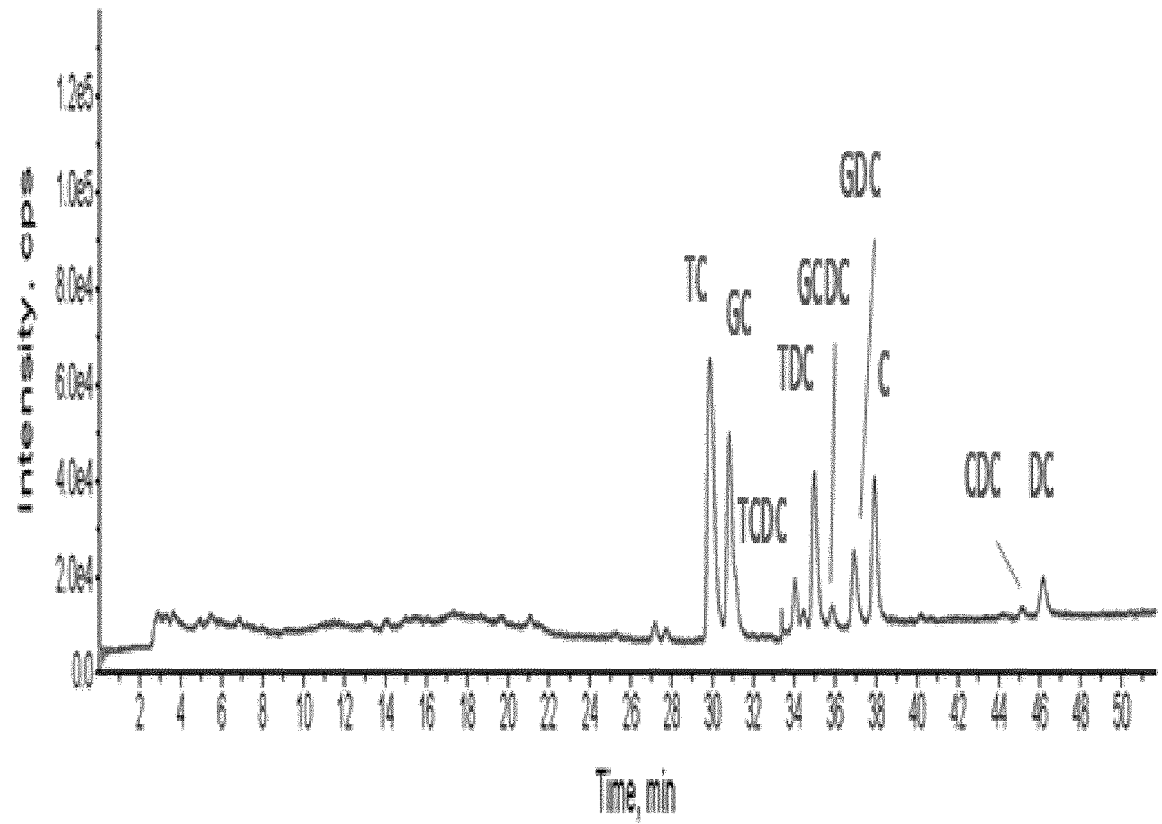

FIGS. 3A to 3C: impact of LjLa1 supernatant on bovine bile composition, as shown by total ion chromatograms detected by LC-MS of the SPE-treated samples corresponding to an incubation of the bile for 24 h at 37° C. with either KM medium alone (FIG. 3A), LjLa1 supernatant (FIG. 3B) or heat-treated LjLa1 supernatant (FIG. 3C). Metabolic profiles were established, from which the main components were identified using Metlin (Smith et al., 2006) or LMSD (Sud et al., 2007) databases, or from their MS/MS fragmentation pattern. TC: taurocholate, GC glycocholate, TCDC: taurochenodesoxycholate, TDC: taurodesoxycholate, GCDC: glycochenodesoxycholate, GDC: glycodesoxycholate, C: cholate, CDC: chenodesoxycholate, DC: desoxycholate.

Figure 4A:
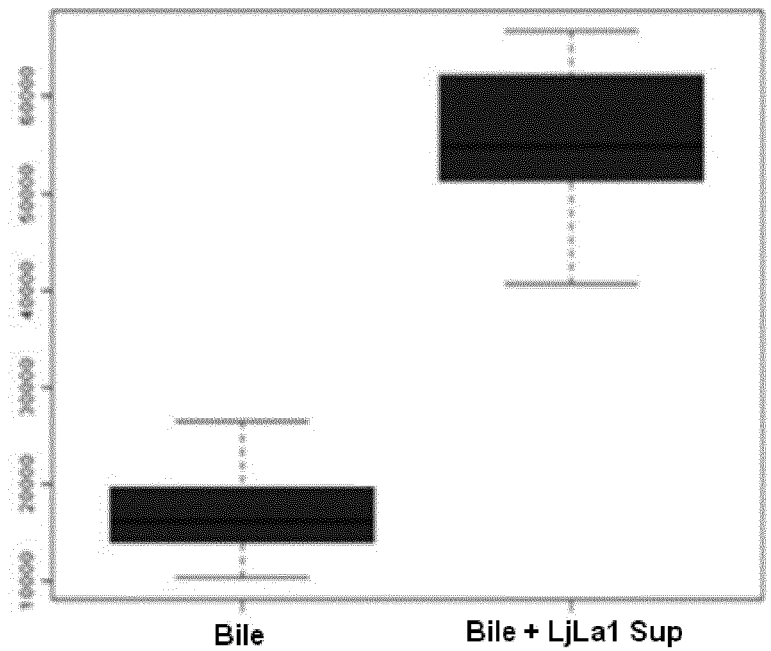
Figure 4B:
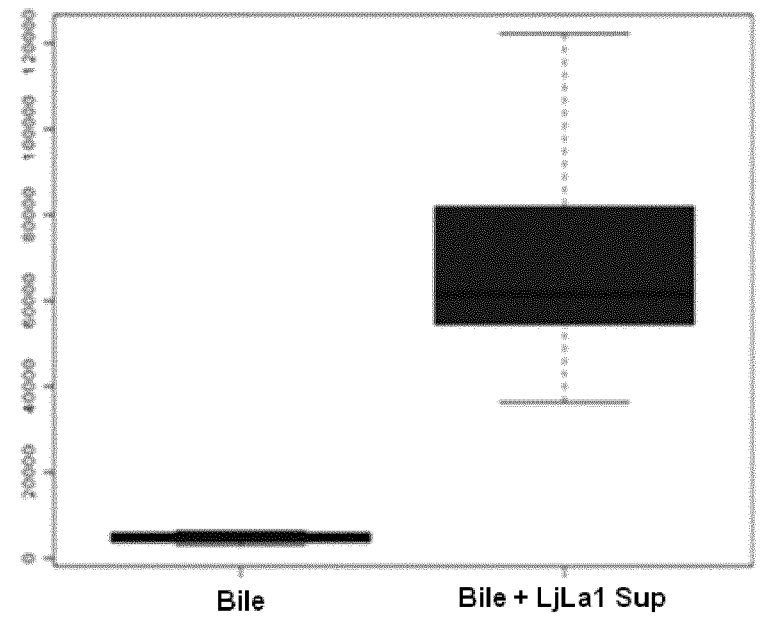

FIGS. 4A and 4B: Increase of non-conjugated salts cholate and deoxycholate content after treatment of bile with LjLa1 supernatant. FIGS. 4A and 4B represent boxplot showing the relative intensity of cholate (C) and desoxycholate (DC) for the bile incubated in the absence (left) presence (right) of LjLa1 supernatant.

Figure 5A:
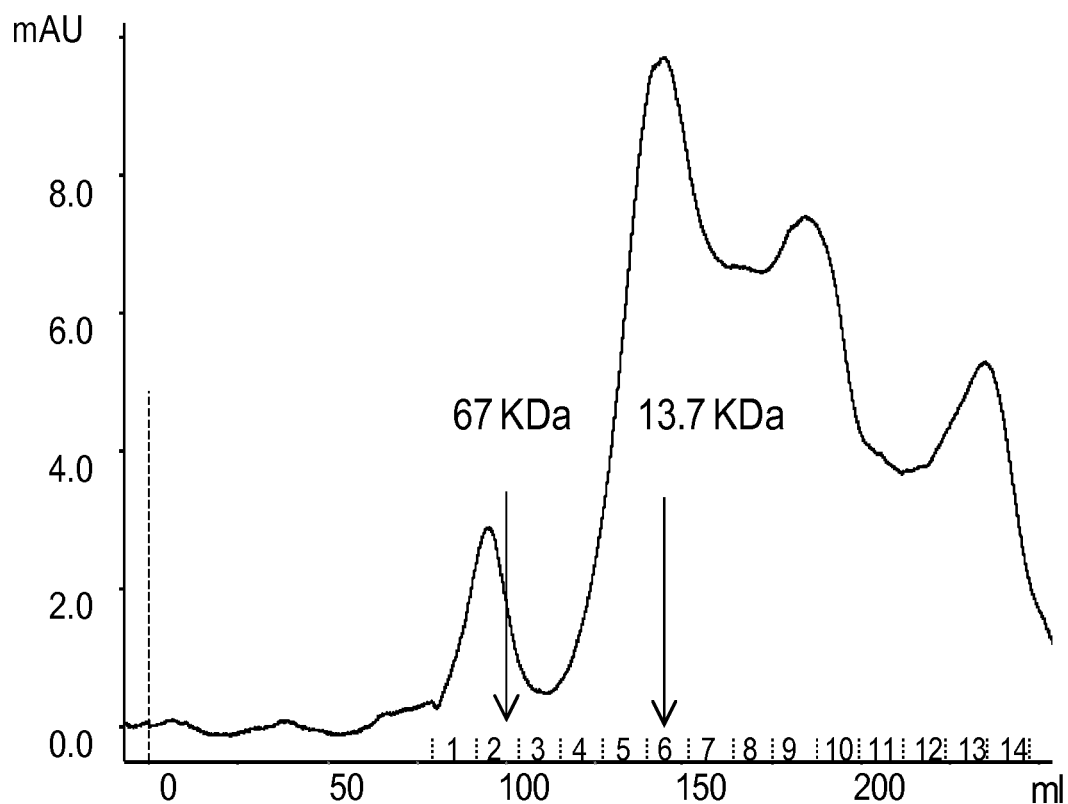
Figure 5B:
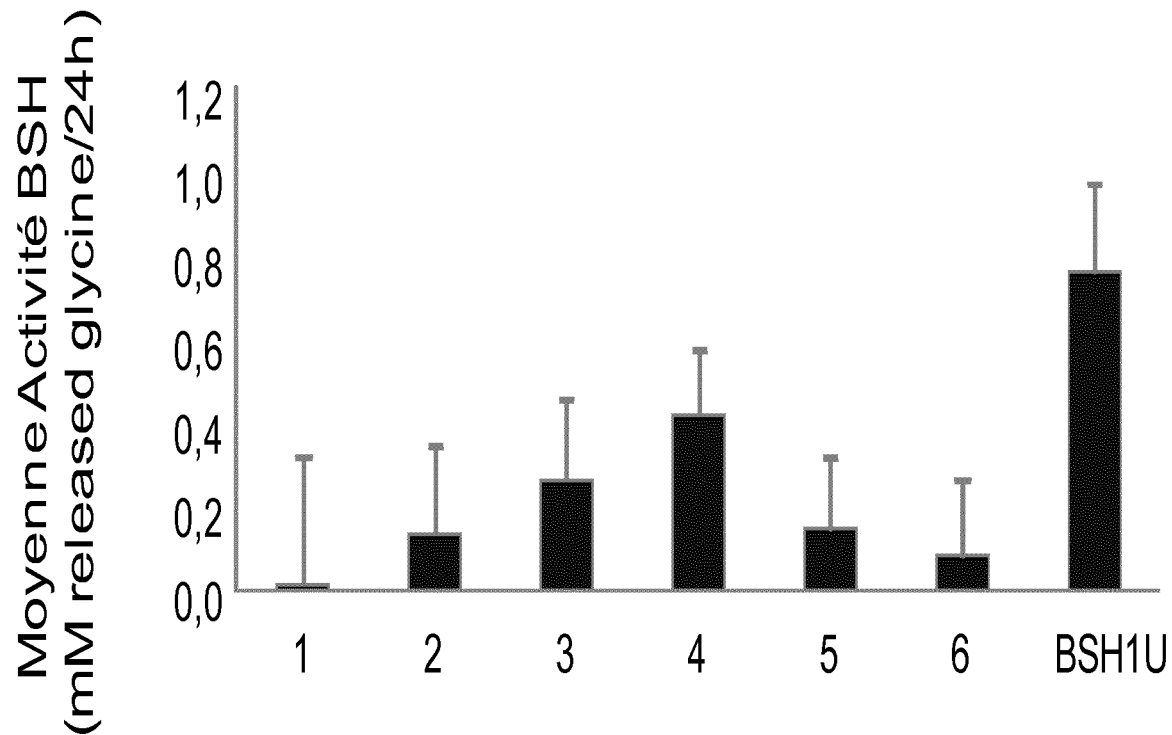
Figure 5C:
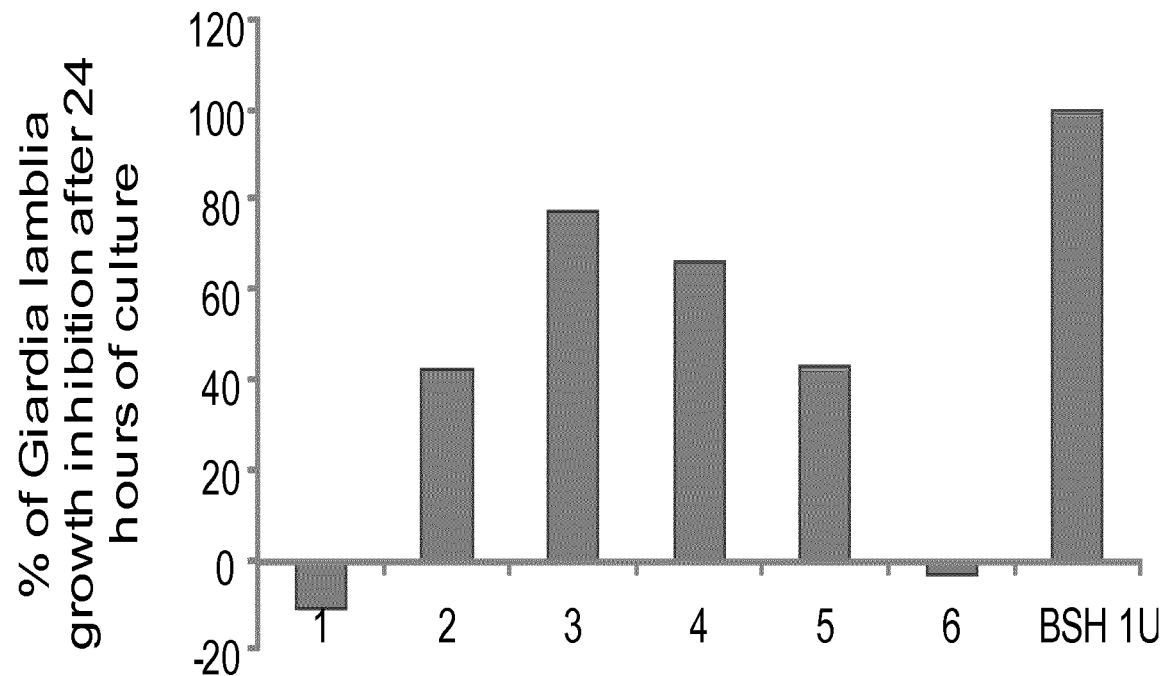

FIGS. 5A to 5C: *G. lamblia* growth inhibitory activity and BSH activity co-eluate in the same fractions after separation of LjLa1 supernatant by gel filtration chromatography. FIG. 5A: Chromatography profile. FIG. 5B: BSH activity measured after 24 h of incubation of GDC (2.4 g/l) with gel filtration fraction collected. FIG. 5C: *G. lamblia* growth inhibitory activity after 24 h of incubation with gel filtration chromatography fractions in presence of GDC (0.2 g/l).

Figure 6:
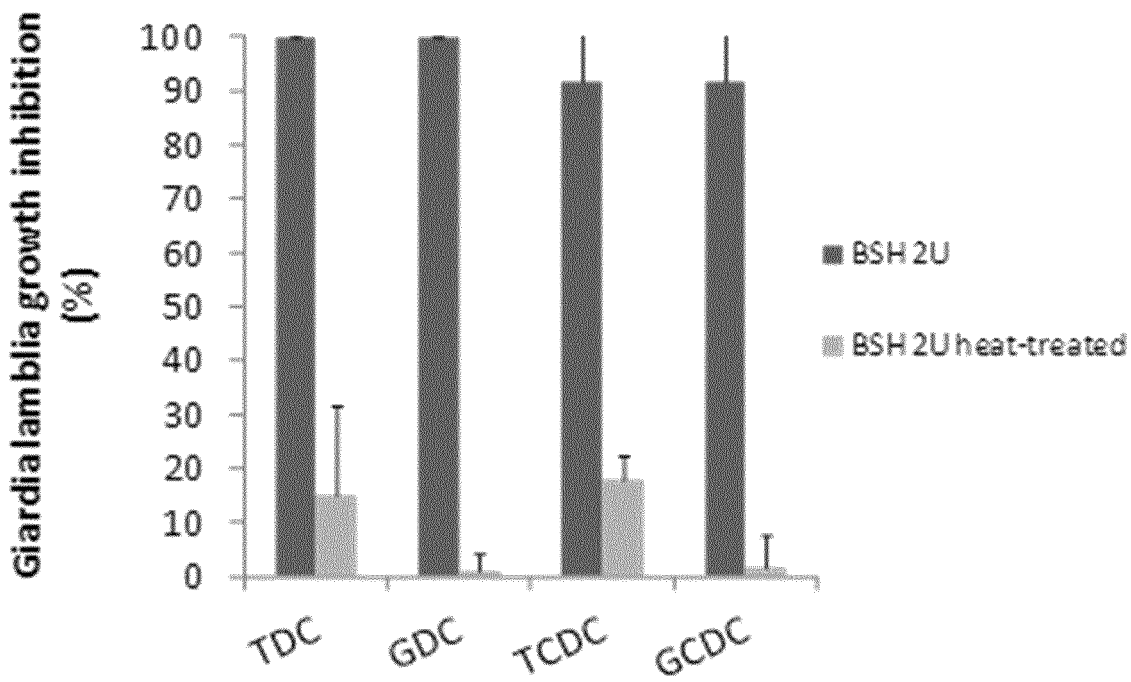

FIG. 6: Inhibition of *Giardia lamblia* growth by enzymatically active *C. perfringens* BSH in the presence of glycine—(GDC, GCDC) or taurine—(TDC, TCDC) conjugated bile salts. Commercial *C. perfringens* BSH, enzymatically active (dark bars) or inactivated (light bars) by a heat-treatment (100° C., 5 min) was added to *G. lamblia* growth medium. GDC: glycodesoxycholate, GCDC: glycochenodesoxycholate, TDC: taurodesoxycholate, TCDC: taurochenodesoxycholate.

FIGS. 7A to 7D: Measurement of *G. lamblia* inhibition by flow cytometry.

Figure 8:
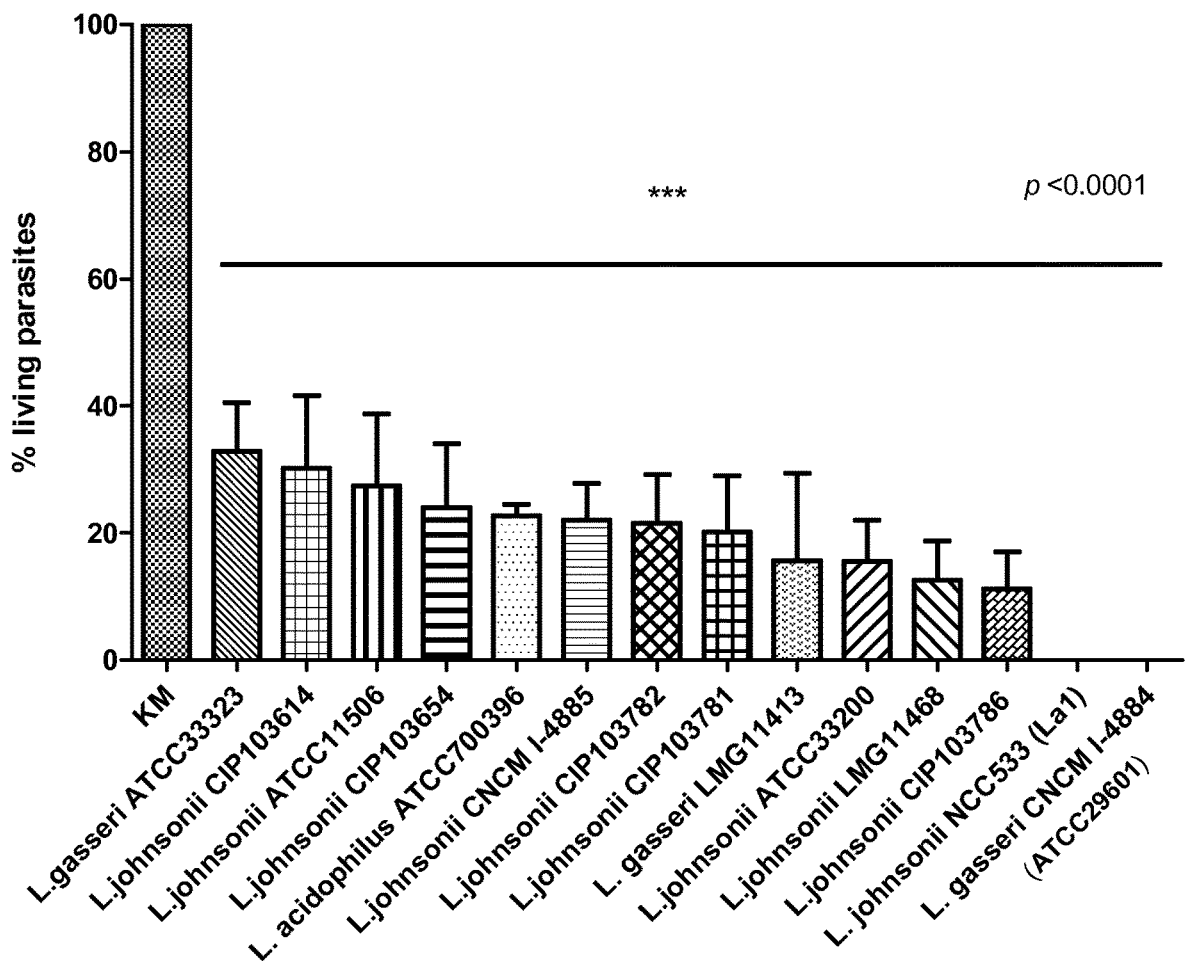

FIG. 8: Percentage of living *G. lamblia* parasites when cultivated in the presence of varying *Lactobacillus* strains.

Figure 9:
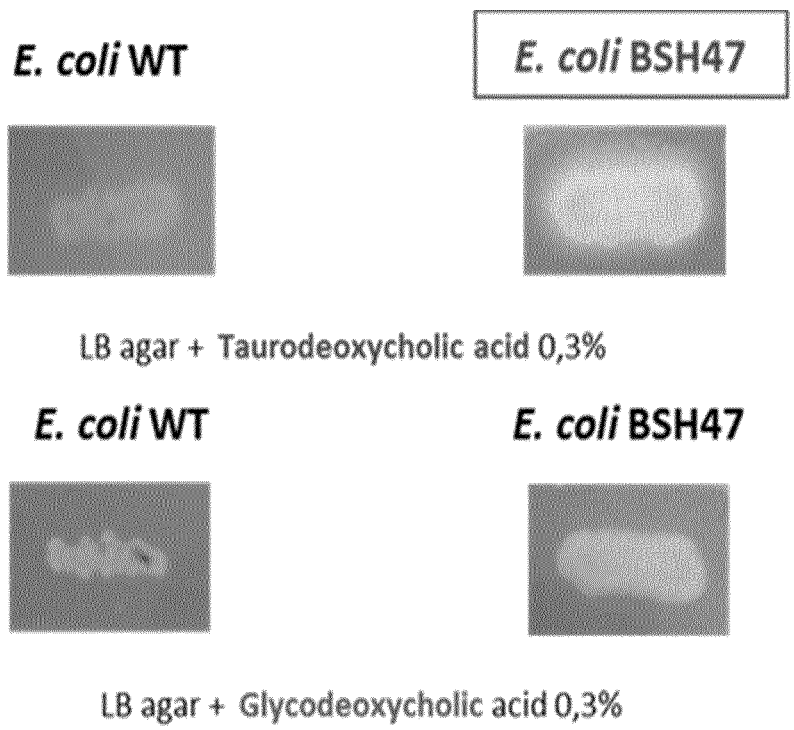

FIG. 9: Enzymatic activity of recombinant BSH-47 produced in *E. coli*. *E. coli* wild type or *E. coli* secreting BSH-47 were incubated in the presence of taurodeoxycholic acid 0.3% (upper panels) or in the presence of glycodeoxycholic acid 0.3% (lower panels).

Figure 10:
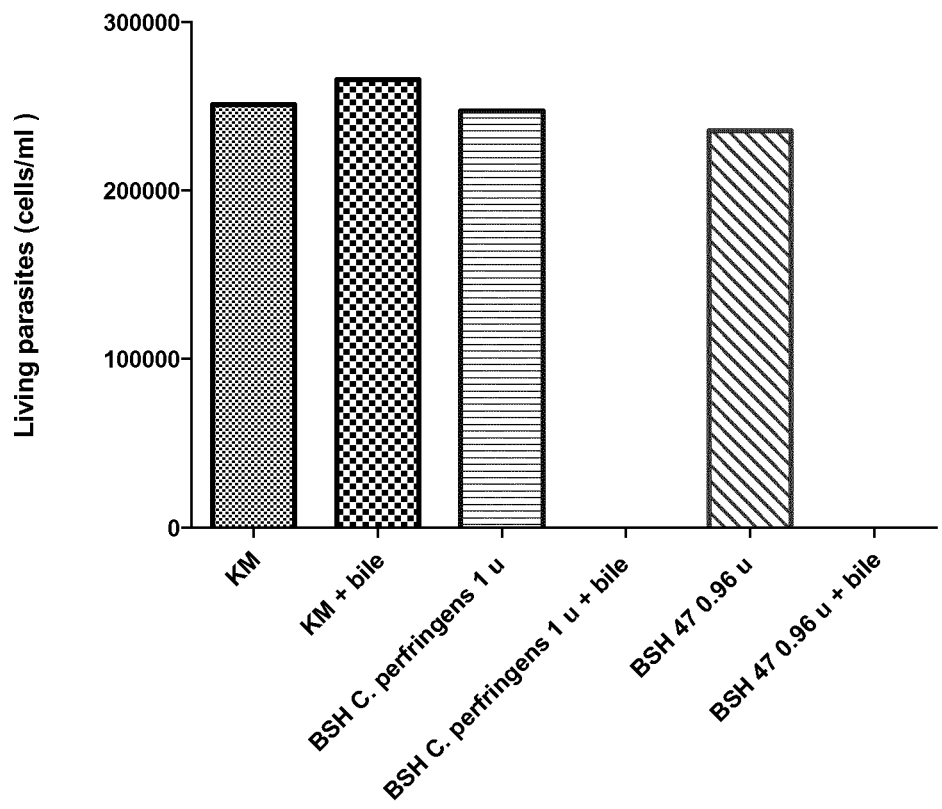

FIG. 10: Histogram representing the number of living *Giardia* parasites (in cells per ml) after incubation with (from left to right) medium, medium and bile, *C. perfringens* BSH (1U), *C. perfringens* and bile, recombinant BSH-47, recombinant BSH-47 and bile.

Figure 11A:
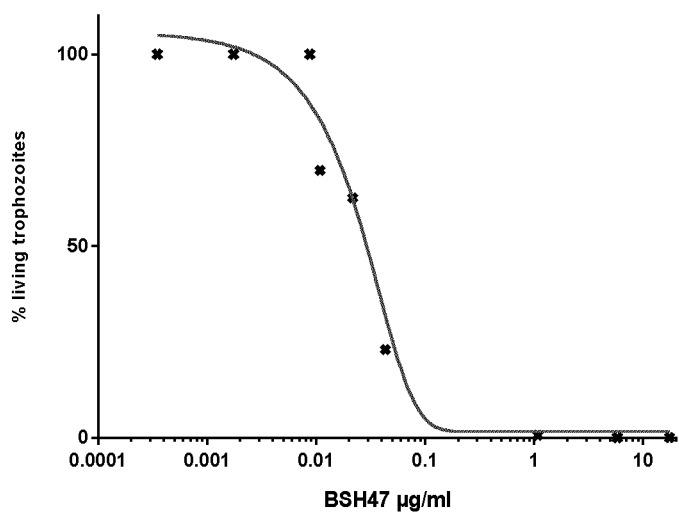
Figure 11B:
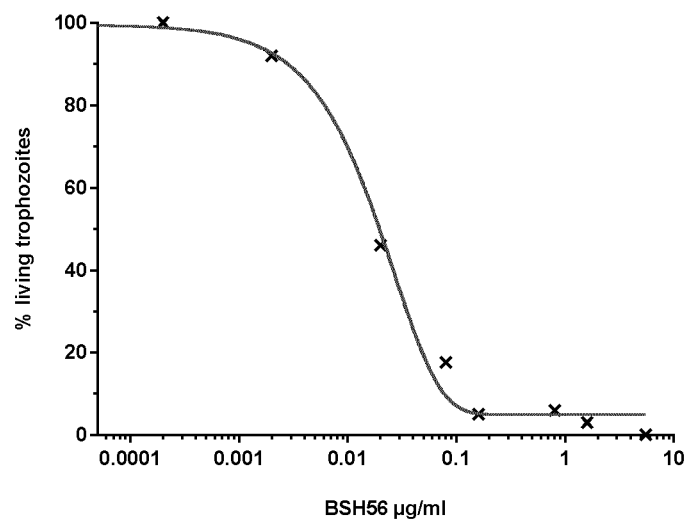

FIGS. 11A and 11B: Inhibition of *Giardia lamblia* growth by enzymatically active recombinant BSH from LjLA1 in the presence of bovine bile (0.6 g/L) after 20 h of incubation. FIG. 11A represents the inhibition of *G. lamblia* growth by recombinant BSH-47. FIG. 11B represents the inhibition of *G. lamblia* growth by recombinant BSH-56.

Figure 12A:
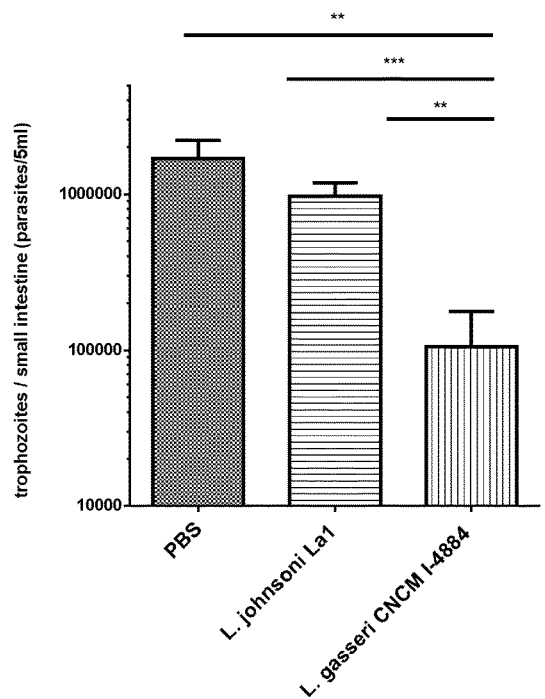
Figure 12B:
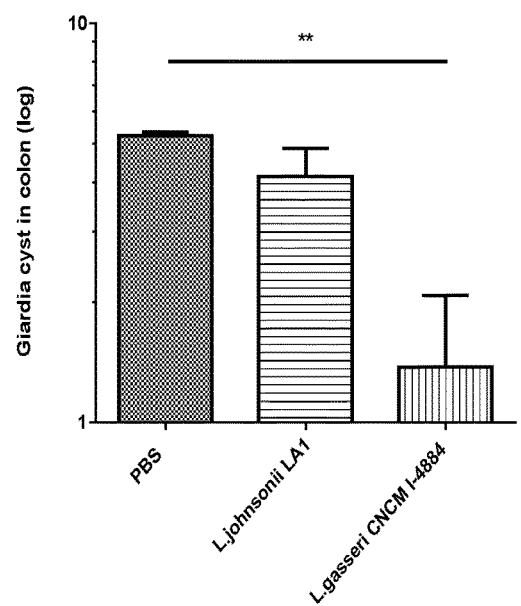

FIGS. 12A and 12B: *G. lamblia* cysts or trophozoïtes counts after administration to animals. Newborn mice received either PBS, LjLa1 or *L. gasseri* CNCM I-4884 by intragastric gavage ($5 \cdot 10^8$ CFU/mice) daily from day 5 before inoculation with the trophozoites of *G. lamblia* WB clone C6 ($10^5$ trophozoites per animal). Gavages were performed until day 15 (n=8 to 12/group). FIG. 12A: *Giardia* trophozoites count in the small intestine. Values are mean±SEM; p<0.05. FIG. 12B: *Giardia* cysts counts in large intestine of mice belonging to different groups. Values are mean±SEM; p<0.05.

Figure 13:
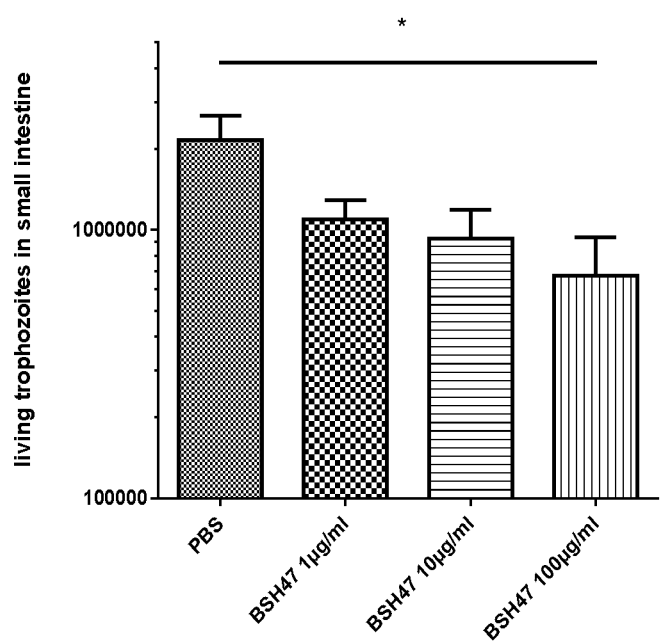

FIG. 13: *G. lamblia* trophozoites count in the small intestine. Mice were challenged with the trophozoites of *G. lamblia* WB clone C6 ($10^5$ trophozoites per animal) at day 10 Animals were treated either with PBS or BSH-47 at 1 μg/ml (0.5 μg per mice), 10 μg/ml (5 μg per mice) or 100 μg/ml (50μg/mice) by daily intragastric gavage until day 15 (n=10 to 11/group). Values are mean±SEM; p<0.05.

EXAMPLES

Example 1: Material and Methods

Products and Preparation of Stock Solutions

Bovine bile solutions (Sigma and Difco) were prepared at 100 mg/ml stock solution in distilled water, filtered at 0.2 µm and stored at −20° C. Pure bile salts (Sigma): glycocholate (GC), taurocholate (TC), glycodeoxycholate (GDC), taurodeoxycholate (TDC), glycochenodeoxycholate (GCDC) and taurochenodeoxycholate (TCDC), bile salt mix (Sigma) or pure corresponding bile salts (Sigma): cholate (C), deoxycholate (DC) and chenodeoxycholate (CDC), and fusidic acid (Sigma) were dissolved in distilled water to 12 mg/ml stock solution, filtered at 0.2 µm and kept at −20° C. Choloylglycine Bile Acid Hydrolase (or Bile Salt Hydrolase, BSH, EC 3.5.1.24) from *Clostridium perfringens* (Sigma) was prepared at 10 U/ml in distilled water (milli-Q grade) and stored at −20° C. Iodoacetic acid (Sigma) was prepared as 0.5 M stock solution in distilled water and frozen at −20° C. Fetal calf serum was from PAA Laboratories, GE Healthcare. The NEFA-C kit used for quantitative determination of non-esterified fatty acids (NEFAs) was from Biolabo (WAKO Diagnostics).

Cell Culture of *Giardia Lamblia*

Trophozoites of *G. lamblia* strains WB (clone C6, ATCC30957) and HP1 (Portland-1, gift of J. Tackezy) were grown as previously described in TYI-S-33 Keiser's medium (KM) with some modifications. TYI-S-33 was adjusted at pH 6.0, supplemented with 10% heat-inactivated fetal calf serum (Paget et al., 2004) and 0.6 mg/ml bovine bile (Carnaby et al., 1994). They were regularly subcultured at a density of $5 \times 10^4$ cells per tube (12 ml) from log phase parasites chilled on ice for 10 min and centrifuged at 700×g, 5 min.

Culture of *Lactobacillus Johnsonii* and Production of Bacterial Supernatant

*L. johnsonii* La1 (LjLa1), CNRZ 1897, NCC533, was kindly provided by Pascal Quénée (INRA Jouy en Josas, Equipe Atalis) and has been isolated from LC1 product in 1996 (Chambourcy, France). LjLa1 stock cultures were kept frozen in MRS Broth media with 15% glycerol. Bacteria were subcultured in MRS Broth medium (Sigma) or modified TYI-S-33 medium (MTYI) (Perez et al. 2001) and incubated anaerobically for 12-18 h at 37° C. Bacteria were subsequently grown in MTYI or KM medium supplemented or not with 10% heat-inactivated fetal calf serum for 12-16 h in the presence or absence of 0.6 mg/ml bovine bile. After centrifugation (3,000×g, 10 min) and 0.2 µm filtration, the pH of the bacterial supernatant was adjusted to 6.0, 6.2, 6.7, 6.9 or 7.2 with 5 N NaOH. Appropriated controls were prepared as follows: lactic acid produced during growth was quantified from aliquots of supernatants (Enzytec™ kit, R-Biopharm) and equivalent amount of lactic acid was added to fresh medium before pH adjustment.

In Vitro *G. Lamblia* Growth Inhibition Assay

One milliliter of trophozoites suspension ($1 \times 10^5$ parasites/ml in KM supplemented with 10% fetal calf serum but without bovine bile) was mixed with either 500 µl of bacterial supernatant or bile salt hydrolase from *C. perfringens* (BSH, 0.2, 1 or 2 U) or appropriate controls in KM or MTYI, in the presence of different concentrations of either bovine bile (0 to 0.6 mg/ml), mixed bile salts (0 to 0.2 mg/ml), conjugated bile salts (0 to 0.2 mg/ml) or deconjugated bile salts (0 to 0.2 mg/ml). Samples were incubated for 24 h at 37° C. and then chilled on ice for 10 min to dislodge trophozoites from tube wall. Living trophozoites (parasites with pear shape showing signs of flagella mobility) were counted using Malassez cell chamber and/or using an hemocytometer. Multiplication factor (i.e. number of total trophozoites at the end of the experiment/number of trophozoites at time zero), survival rate (i.e. (number of living cells/total number of trophozoites)×100) and inhibition percentage (i.e., 100-(number of living cells in the presence of tested compounds/number of living cells in control)×100) were calculated.

Partial Purification of Active Fractions from Bacterial Supernatants by Gel Filtration Supernatants from LjLa1 cultures in MTYI or KM, adjusted to pH 6.0, were concentrated up to 30-fold by ultrafiltration using 10 kDa Centriprep centrifugal filter unit (Millipore). After 0.2 µm filtration, the concentrated supernatants were placed on a Sephacryl S300 column 16/100 (GE Healthcare) previously equilibrated with 20 mM ammonium sulfate, pH 6.0, in a cold room and were eluted with the same buffer at a flow rate of 1.8 to 2.0 ml/min. Twelve effluent fractions of 12 ml were obtained, concentrated 4-fold by ultrafiltration on a 10 kDa Centriprep as described above, and tested for *Giardia* inhibition by classical in vitro growth inhibition assays in the presence of bovine bile or bile salts. Fractions obtained by similar processing of elution buffer alone and control media containing lactic acid (see above) were used as controls. Column calibration was carried out with ribonuclease A (13,700 Da) and bovine serum albumin (67,000 Da).

Characterization of the Active Molecule(s) in LjLa1 Supernatant

Molecular size of active molecule(s) present in the bacterial supernatant was assessed by ultrafiltration using 10 kDa, 30 kDa and 50 kDa Centriprep centrifugal filter units. Thermal stability was tested by heating bacterial supernatant at 90° C. for 10 minutes. Preservation of the LjLa1 supernatant activity upon dialysis was checked by dialyzing twice (for 2 h and 15 h at 4° C., respectively) the supernatant against 100 volumes of KM medium supplemented with 10% FCS or against GKN solution (Perez et al., 2001) (NaCl, 8 g/l; KCl, 0.4 g/l; glucose, 2 g/l; $NaH_2PO_4$, $H_2O$, 0.69 g/l; $Na_2HPO_4$, 1.57 g/l; pH 7.2 to 7.4) using a MWCO 3.5 kDa Spectra-Por dialysis membrane. The dialyzed supernatant was then sterilized by filtration through 0.2 µm membrane and kept frozen at −80° C. before *G. lamblia* inhibition assays.

Finally, biochemical nature of active molecules was determined by preincubating 5-fold concentrated bacterial supernatant obtained by ultrafiltration (>10 kDa) with different proteases coupled to beads. Briefly, proteinase K (Invitrogen) and pronase (Merck) were coupled to CNBr-activated Sepharose™ 4B (GE Healthcare) following manufacturer's instructions. Five milliliter of 5-fold concentrated bacterial supernatant or 5-fold concentrated fresh control medium were incubated for 6 h at room temperature in presence of 100 µl of packed beads previously coupled with 1 mg of each protease. Before growth inhibition assays, beads were removed by centrifugation (4,000×g 5 min). To assess proteases ability to digest proteins from bacterial supernatant, protein content before and after incubation with proteases, was estimated by SDS-PAGE after trichloroacetic acid (TCA) precipitation.

Measurement of Free Fatty Acids

To assess the presence of free fatty acids in the complex medium inducing *Giardia* growth inhibition, FCS, bile and LjLa1 supernatant (LjLa1sn) were analyzed for non-esterified fatty acids (NEFAs) content either alone (FCS, LjLa1sn, bile) or in combination (FCS-bile, FCS-LjLa1sn, bile-LjLa1sn, FCS-bile-LjLa1sn). Concentration of each component was that in the inhibition assay. Samples (0.5 ml) were prepared and kept on ice before being incubated for 24 h at 37° C. in the presence of $4.8 \times 10^4$ trophozoites or without cells. At the end of the incubation period, tubes were chilled on ice, centrifuged at 700×g, 10 min at room temperature, then the supernatant was taken and frozen at −80° C. before NEFAs measurement. Numbers of living and dead trophozoites were determined using a Malassez cell chamber. NEFAs were quantified by using the NEFA-C kit, following manufacturer's instructions. Oleic acid was used as standard and NEFAs were expressed as oleic acid equivalents (Eq).

Bile Salt Hydrolase Activity Assays

After gel filtration, the eluted fractions were concentrated 10-fold by dialysis against 20 mM ammonium acetate buffer containing 2 M sucrose, pH 6.0, using a 3.5 kDa MWCO membrane (Spectrum Laboratories). Glycodeoxycholate (GDC) was used to perform growth inhibition assays and enzymatic assays. BSH activity was monitored by measuring glycine liberation from conjugated bile salt, following the protocol described by Grill et al., (2000). Briefly 100 µl of effluent fractions or BSH 1 unit or elution buffer were mixed with 100 µl of 2.4 g/l of GDC and incubated 24 h at 37° C. Controls were performed in the absence of bile salt or by pre-incubating effluent fractions with 2 mM iodoacetic acid or 30 min at 37° C. To stop the enzymatic reaction, an equal volume of 15% TCA (200 µl) was added and proteins were precipitated by centrifugation at 20,000 g for 15 minutes. 680 µl of 0.3M borate buffer, 1% SDS, pH 9.5 and 80 µl of 0.3% picrylsulfonic acid solution (Sigma) were added to 80 µl of supernatants. Mixtures were incubated for 30 min in the dark and 800 µl of 1 mM HCl were added to stop the reaction. Glycine concentration was measured at 416 nm using an Uvikon spectrophotometer 930 (Kontron Instruments). Standard curve was established with free glycine.

LC/ESI-MS Analysis of Modifications of Bile Components by LjLa1 Supernatants

125 µl of bile-containing culture media of *G. lamblia* (KM, pH 6.0, with 2 g/L bovine bile) and 125 µl of LjLa1 supernatants prepared from a bacterial culture in KM medium supplemented with 10% fetal bovine serum, adjusted at pH 6.0 were mixed and incubated overnight at 37° C. Two different bile batches (B1 and B2) and two different bacterial supernatants (S1 and S2) were tested. The samples were diluted 4-fold in Milli-Q water and subjected to solid-phase extraction (SPE) using Oasis® HLB cartridges (30 mg solid phase). After conditioning with 3 ml methanol and 3 ml Milli-Q water, the cartridges were loaded with 1 ml of 4-fold diluted sample, washed with 2 ml Milli-Q water and eluted with 2 ml methanol. The eluted fractions were dried under vacuum and resuspended in 500 µl Milli-Q water/acetonitrile 90:10 (v/v). Five µl of each resuspended sample was analyzed by LC/ESI-MS on a Ultimate U3000 chomatographic system (Thermo) connected to a Q-STAR Pulsar Qq-TOF mass spectrometer equipped with an ionspray source (AB Sciex). The LC separation was achieved on a Interchrom Strategy C18-2 micro column (5 µm, 150×1 mm, 100 Å, Interchim). The elution gradient was 10% mobile phase B (acetonitrile) to 70% B against mobile phase A (5 mM ammonium formate/formic acid, pH 6) over 45 min, at a flow rate of 40 µl/min. The MS data were acquired in negative mode, in the range m/z 250-1200. Each LC/ESI-MS experiment was conducted twice. Data-dependant LC/ESI-MS/MS experiments were also conducted on each sample, alternating 1-second full-scan MS followed by two 2-second product ion collision induced dissociation (CID) of the major ions detected at the first step, using a −50 V collision voltage. Each raw LC/ESI-MS data was converted into Network Commun Data Form (NetCDF) using the translation tool provided by AB Sciex. The data were processed with XCMS (Smith et al. 2006), a software implemented in the freely available R environment (www.r-project.org), which allows automatic retention time alignment, matched filtration, peak detection and peak matching.

Protein Precipitation 0.1% of sodium lauroyl sarcosinate (NLS, Sigma) was added to bacterial supernatants. After mixing, TCA (trichloroacetic acid) was added to a final 7.5% concentration, and the solution was precipitated on ice overnight. The mixed protein-detergent precipitate was collected by centrifugation (10,000×g, 10 min, 4° C.). The supernatant was carefully removed and the pellet washed twice with 2 ml of precooled tetrahydrofuran (Sigma). Finally, the pellet was dissolved in 0.4 ml extraction solution (7 M Urea, 2 M Thiourea, 4% CHAPS, 5 mM Tris(carboxyethyl)phosphine) (Rabilloud et al., 2009).

Proteomic Analysis of LjLa1 Supernatant

TCA precipitated LjLa1 supernatant was resuspended in 8 M urea in 20 mM TEAB (triethylammonium bicarbonate) and incubated for 1 h at room temperature (RT) with 20 mM DTT (Dithiothreitol), then with 50 mM IAA (iodacetamide) and incubated for a further hour at RT in the dark. The sample was incubated with 0.05 UA of endoproteinase Lys-C (Wako Pure Chemical Industries, Osaka, Japan) for 18 h at RT. Trypsin (Promega) digestion was performed with 2 µg of enzyme during 4 h at RT and terminated with TFA (trifluoroacetic acid), final concentration of 0.5%. The sample was passed sequentially through two home-made Poros Oligo-R3 (PerSeptive Biosystems, Framingham, USA) microcolumns packed (±1 cm) on p200 tips over 3MM C18 material plug. Loaded resin was washed with 100 µl 0.1% TFA and peptides were eluted with 100 µl 70% acetonitrile (ACN)/0.1% TFA, then 20 µl 100% ACN. The sample was desalted, dried down, resuspended in 50% ACN and 10% was collected to amino acid analysis using a Biochrom 30 amino acid analyzer (Biochrom, Cambridge, U.K.), then dried and stored at −80° C. again until analysis.

Samples (3 µg per run) were analyzed by an EASY-nano LC system (Proxeon Biosystems, Odense, Denmark) coupled online to an LTQ-Orbitrap Velos mass spectrometer (Thermo Scientific, Waltham, USA). Peptides were loaded onto a 18 cm fused silica emitter 75 μm inner diameter) packed in-house with reverse phase capillary column Repro-Sil-Pur C18-AQ 3 μm resin (Dr. Maisch GmbH, Germany) and eluted using a gradient from 100% phase A (0.1% formic acid) to 35% phase B (0.1% formic acid, 95% acetonitrile) for 180 min, 35% to 100% phase B for 5 min and 100% phase B for 8 min (a total of 23 min at 250 nl/min). After each run, the column was washed with 90% phase B and re-equilibrated with phase A. Mass spectra were acquired in positive mode applying data-dependent automatic survey MS scan and tandem mass spectra (MS/MS) acquisition. Each MS scan in the orbitrap (mass range of m/z of 400-1800 and resolution 100,000) was followed by MS/MS of the fifteen most intense ions in the LTQ. Fragmentation in the LTQ was performed by collision-induced dissociation and selected sequenced ions were dynamically excluded for 25 s. Raw data were viewed in Xcalibur v.2.1 (Thermo Scientific, Waltham, USA) and data processing was performed using Proteome Discoverer v.1.3 (Thermo Scientific, Waltham, USA). Generated raw files were submitted to searching using Proteome Discoverer with an in house Mascot v.2.3 algorithm against database of proteins predicted from the *L. johnsonii* isolates NCC533 and FI9785 and the *L. johnsonii* prophage Lj965. Contaminant proteins (several types of human keratins, BSA and porcine trypsin) were also added to the database and all contaminant proteins identified were manually removed from the result lists. The searches were performed with the following parameters: ms accuracy 10 ppm, MS/MS accuracy 0.6 Da, trypsin digestion with one missed cleavage allowed, fixed carbamidomethyl modification of cysteine and variable modification of oxidized methionine and N-terminal protein acetylation. Number of proteins, protein groups and number of peptides were filtered for False Discovery Rates (FDR) less than 1% and only peptides with rank 1 and minimal of 2 peptides per proteins were accepted for identification using Proteome Discoverer (Charneau et al., 2007); Queiroz et al. 2013).

Example 2: *L. Johnsonii* La1 Supernatant Inhibitory Effect is Dependent Upon Bovine Bile and More Specifically Upon Bile Salts Most media previously described to support *G. lamblia* growth commonly contains bile as a supply for parasite cholesterol and fatty acids requirements (Farthing et al., 1985, Gillin et al., 1986, Halliday et al., 1995).

In our hands, *G. lamblia* trophozoites growth can be observed in a common medium (KM-FCS) in the absence of bovine bile. Moreover, recommended bile concentrations (0.75 mg/ml, Perez et al., 2001) appeared to affect trophozoites growth when added to the common KM-FCS (FIG. 1A). Interestingly, LjLa1 inhibitory effect was observed only in presence of bile. No inhibitory effect by the supernatant could be observed in the absence of bovine bile, even after 24 h of culture (FIG. 1A). In presence of 0.75 g/L of bovine bile (Perez et al., 2001), *G. lamblia* trophozoites growth was slightly impacted by bacterial supernatant after 10 hours of contact but largely affected after 24 hours of contact ($9 \cdot 10^4$ and $1 \cdot 10^4$ trophozoite/ml, respectively, FIG. 1A). Thus, the 24 h incubation time-period was retained for all subsequent inhibitory growth assays.

Maximum inhibitory effects of LjLa1 supernatant on parasite growth was observed either in the presence of 0.6 g/L complete bovine bile or in the presence of 0.032 g/L bile salts (96.3% and 75% of inhibition, respectively, by comparison with controls containing similar amount of lactic acid and bile or bile salts, FIG. 1B). Similar effects were observed using two isolates of *G. lamblia* (WB and HP1), two different commercial origins of bovine bile and two different media compatible with bacteria and parasite growth: MTYI (Perez et al., 2001) and KM-10% FCS (Data not shown). Subsequent inhibition in vitro assays were thus performed using 0.6 g/L of bovine bile.

Example 3: Characterization of the Inhibitory Activity

To biochemically characterize the inhibitory compounds present in the LjLa1 supernatant, this supernatant was treated with immobilized enzymes prior to contact with parasites. Parasite growth inhibition was abolished by proteinase K and pronase treatments of the supernatant, suggesting involvement of inhibitory factor(s) of peptidic nature (FIG. 2A). Heat-treatment also led to inactivation of the inhibitory properties of the bacterial supernatant (FIG. 2A). Additionally, in a pH range similar to the ones experienced by *G. lamblia* in vivo (Biagini et al., 2001), a strong influence of pH on the inhibitory reaction was noticed, with highest inhibition occurring at pH 6.2 (FIG. 2B).

Moreover, as Pridmore et al. (2004) demonstrated that the LjLa1 anti-*Salmonella* activity is mediated by the toxic hydrogen peroxide molecule $H_2O_2$ and can be abolished by a pretreatment with catalase, we checked whether treatment of LjLa1 supernatant with catalase might prevent its anti-*Giardia* effect. As it can be seen in FIG. 2A, catalase pretreatment only slightly affected the inhibitory activity of the LjLa1 supernatant on *G. lamblia* (FIG. 2A), invalidating the role of $H_2O_2$ in *Giardia* growth inhibition.

Example 4: *Giardia* Growth Inhibition by LjLa1 Supernatant is not Clue to Free Fatty Acids To assess whether *G. lamblia* growth inhibition by LjLa1 supernatant might be due to toxic free fatty acids as demonstrated in previous reports (Rohrer et al. 1986), FCS, bile and LjLa1 supernatant were analyzed for non-esterified fatty acids (NEFAs) content either alone or in combination, using the NEFA-C methodology (WAKO diagnostics). The different samples were incubated for 24 h at 37° C. with or without *G. lamblia* trophozoites and the cell supernatants were analyzed for NEFAs. Survival and growth of the parasites in those different conditions were determined.

The following Table 1 represents the analysis of non-esterified fatty acids involvement in *Giardia* inhibition. The different components of the *Giardia* culture medium (FCS 10% and/or bile 0.5 g/L), as well as LjLa1sn, were analyzed either alone or in combination for NEFA content after 24 h of incubation at 37° C. Incubation was performed with or without *G. lamblia* trophozoites ($9.6 \times 10^4$/ml). Survival and multiplication of *G. lamblia* after 24 h in those different media were determined. Parasite multiplication was expressed as the number of total trophozoites after 24 h of incubation/number of trophozoites at time zero of incubation (i.e. multiplication factor). Trophozoite survival rate after 24 h of incubation was expressed as the (number of living cells/total number of cells)×100.±SD (triplicate).

Supernatants with FCS, LjLa1sn or bile alone displayed NEFAs concentrations of 40.9, 36.3 and 4.5 μM, respectively (Table 1).

TABLE 1

| Incubation medium | NEFAs (μM Eq) | Multiplication factor | Survival rate (%) |
|---|---|---|---|
| KM | 0 | 1.1 | 14.3 |
| KM + FCS | 40.9 | 3.3 | 89.8 |
| KM + bile | 4.5 | 0.7 | 0 |
| KM + LjLa1sn | 36.4 | 1.2 | 71.6 |
| KM + FCS + bile | 95.4 | 2.3 | 93.8 |
| KM + FCS + LjLa1sn | 68.2 | 2.1 | 87.5 |
| KM + bile + LjLa1sn | 50.0 | 0.8 | 0 |
| KM + FCS + bile + LjLa1sn | 140.9 | 0.8 | 0 |

The amount of NEFAs was doubled (95.4 μM) by co-incubation of the bile with serum suggesting enzymatic release of NEFAs. However, equal amounts were found at time zero and time 24 h of the co-incubation (not shown), indicating that fatty acids were not released in a time-dependent manner. It was hypothesized that the high amount of NEFAs might result from a detergent-like action of the bile on serum lipids, possibly improving accessibility of NEFAs to the NEFA-C kit reagents. The highest amount of NEFAs (140.9 μM) was measured upon co-incubation of FCS with bile and LjLa1sn, as could be expected by summing their respective NEFAs contents. Incubation with G. lamblia had no noticeable effect on the NEFA content of the various samples (Data not shown).

Normal growth of G. lamblia (multiplication factor: 3.34, Table 1) was observed in the presence of 10% FCS alone. Trophozoites did not survive in KM medium containing only bile, whereas most of them (~70%) were still alive although they did not develop when incubated in KM with LjLa1 supernatant, most probably due to the low concentration of FCS in LjLa1 supernatant. Remarkably, trophozoites survival was abolished upon addition of bile to LjLa1sn although the same concentration of FCS is present, indicating the presence of inhibitory elements. By comparing NEFAs contents of the different media, it appeared that NEFAs could hardly be responsible for parasite death. Indeed, more NEFAs were found in the KM+FCS+bile or KM+FCS+LjLa1sn media (95.4 and 68.2 μM of NEFAs respectively), which allowed parasite survival, than in the KM+bile+LjLa1sn medium (50.0 μM of NEFAs) which induced the death of all the parasites. This indicated that the concomitant addition of bile and bacterial supernatant rather than high level of NEFAs is lethal to Giardia and is responsible for the killing effect observed in the presence of FCS, bile and LjLa1 supernatant.

Example 5: Characterization of LjLa1 Supernatant Inhibitory Activity

The LjLa1 Supernatant Inhibitory Activity is Due to ~30 kDa Molar Mass Factor(s)

Fractionation experiments indicated that the inhibitory activity in LjLa1 supernatant was due to molecule(s) bigger than 10 kDa, since fraction >10 showed a high G. lamblia inhibitory activity compared to the fraction <10 kDa (FIG. 2C). By performing a 30 kDa threshold fractionation, we found that the inhibitory activity concentrated mostly in the >30 kDa fraction (inducing 66% of Giardia growth inhibition, FIG. 2C), however moderate inhibitory effect (~40%) was also observed with the <30 kDa fraction, which led us to propose that the molar mass(es) of the active molecule(s) are close to this threshold. In good accordance with this, 50 kDa threshold fractionation of the LjLa1sn was unable to segregate the inhibitory activity, i.e. 50% and 48% of Giardia growth inhibition were induced by the <50 kDa and >50 kDa fractions, respectively (FIG. 2C), indicating that inhibitory protein(s) molar mass is smaller than 50 kDa.

Small Compounds are Not Primarily Involved in LjLa1sn Inhibitory Activity

It has been reported that molecule(s) smaller than 1 kDa (Perez et al., 2001) would be involved in the giardiacidal activity of the LjLa1 supernatant, in contradiction with our findings of a ≥30 kDa molecule(s). The possibility that dialysis against GKN buffer as used in Perez's report might somehow inhibit the activity has been checked. Several points were checked. At first, because the pH of the GKN buffer is 7.4 and the LjLa1sn inhibitory activity is inactivated at pH above 7.0 (FIG. 2B), pH of the KM medium was checked after supplementation with 10% FCS and 25% GKN. The pH was found to be increased to 6.5, hence not expected to inactivate LjLa1 supernatant (FIG. 2B). Second, to assess whether small component(s) might be involved in the inhibitory effect, the bacterial supernatant was dialyzed using a 3.5 kDa molecular weight cut-off membrane against both KM 10% FCS and GKN buffer. As can be seen in the following Table 2, parasite killing activity of the LjLa1 supernatant in the presence of bile was fully recovered after dialysis, whatever the dialysis solution. Table 2 represents dialysis through low MW cutoff membrane does not inactivate inhibitory activity of LjLa1 supernatant (LjLa1sn). KM-FCS medium, bile (0.5 g/L) and LjLa1sn, either alone or in combination, were dialyzed against GKN buffer or KM-FCS, and then tested for G. lamblia trophozoites growth. Values are mean of two independent experiments performed in duplicate.

TABLE 2

|  | KM + FCS | KM + FCS + GKN | KM + FCS + LjLa1sn | KM + FCS + LjLa1sn dialysed against KM-FCS | KM + FCS + LjLa1sn dialysed against GKN |
|---|---|---|---|---|---|
| Multiplication factor | 3.82 | 2.60 | 3.24 | 3.68 | 2.44 |
| Survival rate (%) | 93.7 | 92.3 | 88.3 | 90.2 | 89.3 |

TABLE 2-continued

|  | KM + FCS + bile | KM + FCS + bile + LjLa1sn | KM + FCS + bile + LjLa1sn dialysed against KM-FCS | KM + FCS + bile + LjLa1sn dialysed against GKN |
|---|---|---|---|---|
| Multiplication factor | 2.28 | 1.16 | 1.46 | 0.8 |
| Survival rate (%) | 92.9 | 0 | 0 | 0 |

This indicates on one side that no element crucial to activity is lost upon dialysis and on the other side that the GKN buffer is not inhibitory to the LjLa1 supernatant activity. Also, it can be noticed from Table 2 that addition of 25% GKN buffer to KM-FCS does not affect parasite survival but slows down its development (multiplication rate of 2.60 in the presence of GKN versus 3.82 in the absence of GKN).

Example 6: Impact of LjLa1 Supernatant on Bile Composition

Since concomitant addition of bile and LjLa1sn to the culture medium leads to inhibition of G. lamblia growth, we assessed whether bile composition might be modified by LjLa1 supernatant. Bile composition after 24 h of incubation with LjLa1sn was investigated by mass spectrometry (FIGS. 3A-B). Impacted molecules were identified by their MS/MS fragmentation pattern. Comparison of bile salts profiles showed a decrease of conjugated salts (GC, TC, GDC, TDC, GCDC, TCDC) in favor of non-conjugated salts. Cholate and desoxycholate were the mainly statistically enhanced non-conjugated salts when bile was incubated with LjLa1 supernatant (FIG. 4) and in a minor proportion chenodesoxycholate. These modifications were not observed in presence of heat-treated bacterial supernatant (FIG. 3C).

Example 7: Impact of Deconjugated Bile Salts on G. lamblia Trophozoïtes Growth

The inhibitory effects toward G. lamblia growth of pure bile salts (cholate, desoxycholate and chenodesoxycholate) conjugated to glycine or taurine, or their deconjugated counterparts were investigated in the presence or the absence of LjLa1 supernatant (Table 3, FIG. 5). In the absence of LjLa1sn, glycyl- or tauryl-conjugated salts as well as deconjugated cholate showed no apparent toxicity at the concentrations tested ($IC_{50}$ values>500 µM). In contrast, the deconjugated salts DC and CDC exhibited inhibitory effects on trophozoites growth with $IC_{50}$ values of 132 µM (DC) and 147 µM (CDC) respectively. Interestingly, in the presence of LjLa1 supernatant, the conjugated bile salts $IC_{50}$ values felt to a range of values similar to those measured for their pure deconjugated counterparts, i.e. 104 µM (GDC), 79 µM (TDC), 110 µM (GCDC) and 115 µM (TCDC) (Table 3 and FIG. 5).

The following table 3 shows conjugated bile salts in association with LjLa1 supernatant (LjLa1sn) as well as deconjugated bile salts prevent the growth of G. lamblia. Various concentrations of taurine- and glycine-conjugated and unconjugated C, DC and CDC bile salts were tested for G. lamblia trophozoites growth inhibition in KM-FCS in the presence or absence of LjLa1sn (bacterial spent culture medium). IC50 values were determined from drug-response curves and expressed as mean+/−SD of at least three independent experiments.

TABLE 3

|  |  |  | With culture medium only IC50 +/− SD (µM) | With bacterial spent culture medium IC50 +/− SD (µM) |
|---|---|---|---|---|
| C and derivatives | C | Cholate | >400 | >400 |
|  | GC | Glycocholate | >400 | >400 |
|  | TC | Taurocholate | >400 | >400 |
| DC and derivatives | DC | Desoxycholate | 132 +/− 12.7 | 117 +/− 12.7 |
|  | GDC | Glycodesoxycholate | >400 | 104 +/− 12.7 |
|  | TDC | Taurodesoxycholate | >400 | 79 +/− 17.3 |
| CDC and derivatives | CDC | Chenodesoxycholate | 147 +/− 14.5 | 118 +/− 21.7 |
|  | GCDC | Glycochenodesoxycholate | >400 | 110 +/− 10.6 |
|  | TCDC | Taurochenodesoxycholate | >400 | 115 +/− 7.7 |
|  | FA | Fusidic acid | 26 +/− 3.7 | nd |

These results suggested that a deconjugating process mediated by LjLa1sn component(s) and producing deconjugated bile salts might be responsible for the inhibitory effect of the association of bile and LjLa1sn. Such hypothesis is in line with the previous observation that fusidic acid, an antibiotic with a bile salt-like chemical structure is toxic to Giardia (see Table 3, $IC_{50}$ value=26 µM) unless conjugated to taurine or glycine (Farthing et al., 1986).

Example 8: Potential Involvement of L. Johnsonii La1 Bile-Salt Hydrolase(s) in Bile-Mediated Giardia Inhibition, and Co-Elution of BSH-Like Activity and Giardia Inhibitory Activity in Aize Fractionation Chromatography of LjLa1 Supernatant It is known that bile salt deconjugating process is mediated by 3-alpha, 7-alpha, 12-alpha-trihydroxy-5-beta-cholan-24-oylglycine/taurine amidohydrolases (EC 3.5.1.24), also named choloylglycine/taurine hydrolases or conjugated bile acid hydrolases (CBAH) or bile salt hydrolases (BSH). These enzymes act on carbon-nitrogen bonds other than peptide bonds, specifically in linear amides, releasing glycine and taurine from conjugated bile salts. In *L. johnsonii* genome, three genes encoding BSH-like enzymes have been predicted (LJ0056 (BSH-56), LJ1147 (BSH-47) and LJ1412 (BSH-12) genes). They are also predicted as secreted proteins by SecretomeP, with theoretical full sizes of 34.9 kDa, 36.3 kDa and 36.6 kDa and secreted sizes of 29.8 kDa, 31.0 kDa and 31.3 kDa (data not shown).

To test the hypothesis of bacterial BSH(s) involvement in *G. lamblia* growth inhibitory activity by LjLa1sn, the bacterial supernatant was fractionated by gel filtration chromatography on Sephacryl S300 column 16/100, and eluted fractions were assayed for parasite inhibition and bile salt deconjugating activity.

A typical elution profile is shown in FIG. 5A. Twelve eluated fractions (FIG. 5A) were tested for *G. lambia* growth inhibition (FIG. 5C) and the most active ones were further tested for BSH-like activity (FIG. 5B). Greatest inhibitory activity was recovered from fractions containing proteins with molecular weight between 13.7 kDa and 67 kDa (FIG. 5A). Those fractions exhibited BSH-like activity (FIG. 5C), as measured by the release of glycine from GDCA. In our experimental conditions, 1 unit of the commercial *Clostridium perfringens* BSH induced the release of 0.76 mM glycine from 2.5 mM GDC within 24 hours. Concomitant elution of inhibitory and BSH activities within similar molecular weight range was observed with LjLa1 supernatants from different culture batches. Our attempts to further purify elements responsible for inhibitory activity and/or BSH-like activity by combining steps of ion-exchange chromatography, hydrophobic interaction chromatography and chromatofocusing were unsuccessful, with a rapid loss of the activities.

Example 9: Deconjugation of Tauryl- and Glycyl-DC and -CDC by *Clostridium perfringens* BSH is Toxic to *G. Lamblia*

To assess capability of BSH enzymes to promote bile-mediated anti-*Giardia* effect, BSH from the bacteria *C. perfringens* was tested for *G. lamblia* growth inhibition in the presence of bile or pure conjugated bile salts. As noted above (Table 3), the glycine or taurine conjugated bile salts, TDC, TCDC, GDC and GCDC have no inhibitory activity on *G. lamblia* growth in KM-FCS culture medium. In contrast, the addition of 2 units of *C. perfringens* BSH to the culture in the presence of those bile salts led to a remarkable parasite growth inhibition within the 24 h of the assay, with inhibition ranges of 95 to 100%, depending upon the conjugated bile salt tested (FIG. 6). Heat inactivation of bacterial BSH (100° C., 5 min) before its addition to the parasite culture led to a dramatic fall of its anti-*Giardia* activity (less than 10% growth inhibition depending upon the conjugated bile salts tested, FIG. 6) indicating that BSH inhibitory activity depends on its enzymatic activity.

Example 10: Mass Spectrometric Identification of Two BSH-Like Enzymes in the LjLa1sn It was then searched whether BSH-like enzymes annotated from *L. johnsonii* La1 genome, and predicted by SecretomeP to be secreted, are indeed released in the extracellular medium. High-resolution mass spectrometry-based proteomic analysis of the LjLa1 extracellular proteins was performed. 3 μg of proteins of LjLa1 supernatants from two independent culture replicates allowed identification of over a hundred of secreted protein groups (data not shown). Amongst them, two of the three predicted BSH were clearly identified in both replicates: LJ1412 (gi|41583570) and LJ1147 (gi|41583360). The following Table 4 shows the identification of two conjugated bile salt hydrolases of *Lactobacillus johnsonii* NCC533 by MS/MS peptide fragmentation using MASCOT stringent search.

TABLE 4

| Accession number[a] | Score[b] | Cov. (%)[c] | unique peptides | total pepides | PSMs | Peptide ion sequence[d] (with at least one peptide ion score > 50) | peptide ion charge[e] | peptide ion (m/z) | Theo. Mass (kDa)[f] | Theo. pI[g] |
|---|---|---|---|---|---|---|---|---|---|---|
| experimental replicate 1 ||||||||||||
| gi|41583570 | 162 | 12.58 | 2 | 2 | 5 | NLANYSNIAPAQPK | 2 | 750.9 | 36.6 | 5.2 |
|  |  |  |  |  |  | AHSPQGNNELSSVT | 4 | 759.1 |  |  |
|  |  |  |  |  |  | NYFHILHSVEQPK |  |  |  |  |
| gi|41583360 | 39 | 12.92 | 3 | 3 | 3 | GLGIAGLNFTGPGK | 2 | 651.4 | 36.3 | 4.9 |
|  |  |  |  |  |  | DLPVTTLHWLMGDK | 2 | 813.4 |  |  |
|  |  |  |  |  |  | NTLVPNADINLYSR | 2 | 795.4 |  |  |
| experimental replicate 2 ||||||||||||
| gi|41583570 | 83 | 12.58 | 2 | 2 | 3 | NLANYSNIAPAQPK | 2 | 750.9 | 36.6 | 5.2 |
|  |  |  |  |  |  | AHSPQGNNELSSVT | 4 | 759.1 |  |  |
|  |  |  |  |  |  | NYFHILHSVEQPK |  |  |  |  |

TABLE 4-continued

| Accession number[a] | Score[b] | Cov. (%)[c] | unique peptides | total pepides | PSMs | Peptide ion sequence[d] (with at least one peptide ion score > 50) | charge[e] | peptide ion (m/z) | Theo. Mass (kDa)[f] | Theo. pI[g] |
|---|---|---|---|---|---|---|---|---|---|---|
| gi\|41583360 | 77 | 8.62 | 2 | 2 | 3 | GLGIAGLNFTGPGK | 2 | 651.4 | 36.3 | 4.9 |
|  |  |  |  |  |  | NTLVPNADINLYSR | 2 | 795.4 |  |  |

[a]Accession number in the NCBI protein database. All accession numbers refer to sequences from *Lactobacillus johnsonii* NCC 533;
[b]Probability-based Mowse score of MASCOT software that evaluates if the peptides subjected to search are the same as those found in the database originated by in silico digestion of a known protein;
[c]Coverage is the percentage of predicted protein sequence covered by matched peptides via MASCOT;
[d]Peptide sequences identified via MASCOT following the experimental peptide masses after parental ion fragmentation. It was required that at least one spectrum should be matched with score of 50 or better to considered the hit;
[e]Doubly- to quintuply-charged ions of selected peptides were analyzed.
[f]Theoretical molecular masses of proteins calculated from amino acid sequences;
[g]Theoretical isoelectric points of proteins calculated from amino acid sequences.

Example 11: Measurement of *G. Lamblia* Inhibition by Flow Cytometry

Figure 7A:
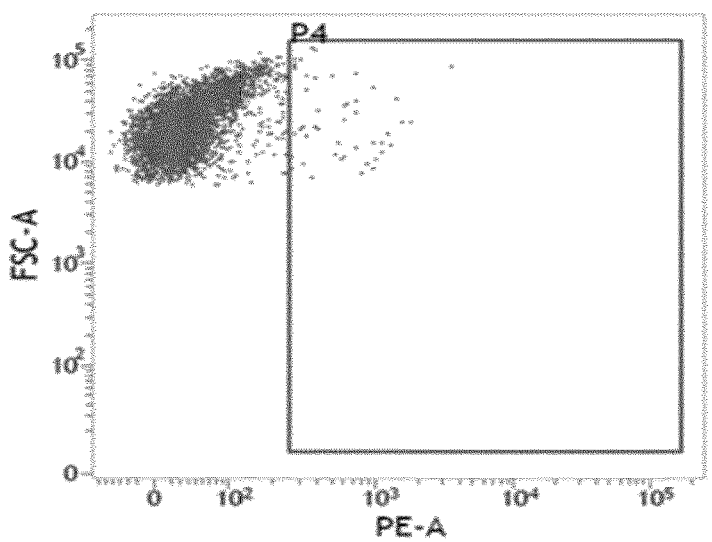
Figure 7B:
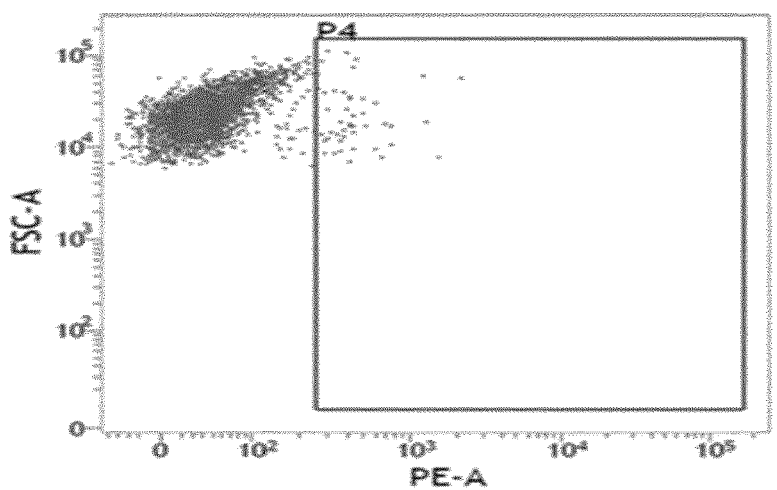
Figure 7C:
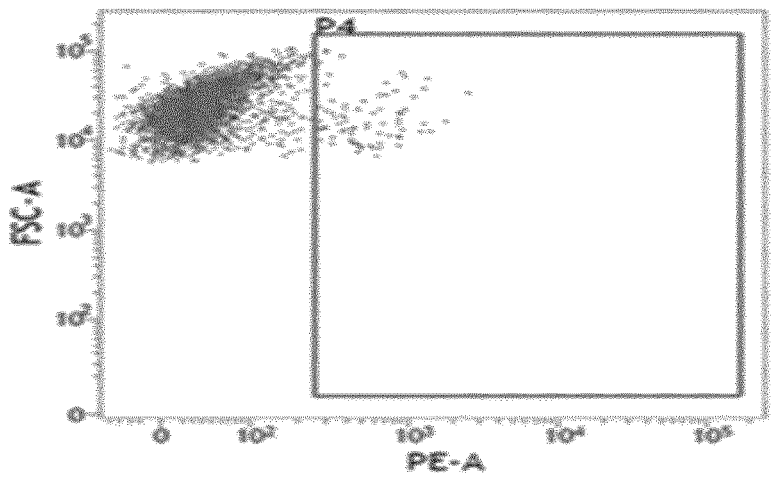
Figure 7D:
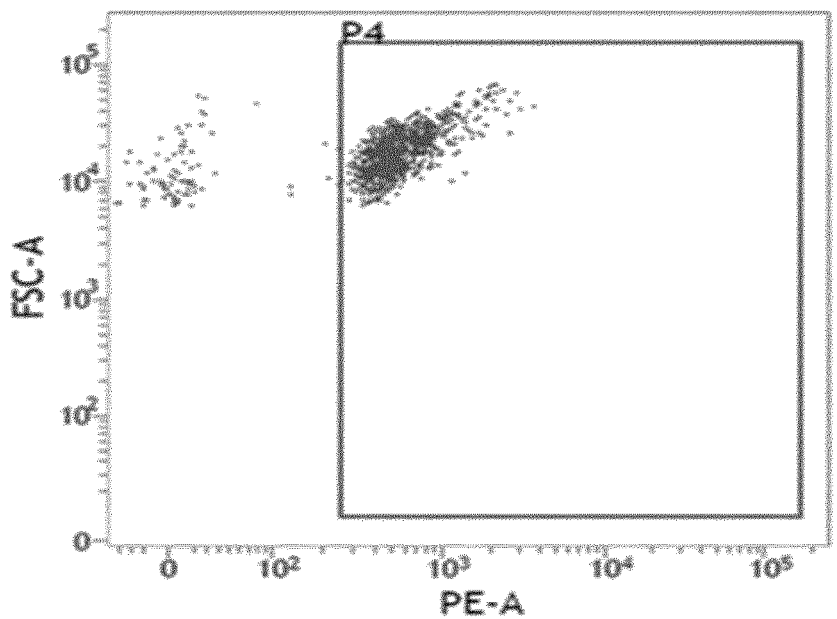

The inhibitory effect of *L. johnsonii* on *G. lamblia* was measured by flow cytometry, as shown in FIGS. 7A to 7E. Propidium iodide, an intercalating agent fluorescing when excited at 540 nm, was used to evaluate *Giardia* cell viability in order to confirm Hemocytometer results. These results showed that, tested separately, neither LjLa1sn nor bovine bile (0.6 g/L) have cell lysis activity. However, in presence of both Ljla1sn and bovine there is a fluorescence shift (FIG. 7E) evincing that bile has a cytotoxic effect on *Giardia* trophozoites (FIG. 7D; FIG. 7E). Flow cytometry allowed us to analyse a higher amount of cells and may be used routinely as a measurement method of *G. lamblia* inhibition. Moreover, this technique has been used for other lactobacilli supernatant (data not shown).

Example 12: Identification of Anti-Giardiasis Lactobacilli Strains

The inhibitory effect on *G. lamblia* growth of different lactobacilli strains was screened (cf. table 5). Bacterial supernatant was co-incubated for 24 h at 37° C. with *Giardia* trophozoite cultures (triplicates), with or without bovine bile (0.6 g/L). Different species of lactobacilli were identified as potent inhibitors of *Giardia lamblia* growth, as *Lactobacillus johnsonii, Lactobacillus gasseri, Lactobacillus acidophilus, Lactobacillus reuteri*. 14 lactobacilli strains showed significant inhibitory effects (ANOVA statistic tests) in presence of bile (FIG. 8) None of the supernatant had an inhibitory effect without bovine bile, confirming that the giardiacidal effect is bile dependent. Table 5 indicates the corresponding internal and official references of the bacterial strains, and bibliographic references.

TABLE 5

| Bacterial strain | ATCC | CIP (*) | LMG (*) | CNCM (*) | Publication |
|---|---|---|---|---|---|
| *L. johnsonii* |  |  |  | I-4885 | Fujisawa et al., 1992 |
| *L. gasseri* | 33323 | 102991 | 9203 T |  | Lauer and Kandler, 1980 |
| *L. johnsonii* |  | 103614 |  |  | Fujisawa et al., 1992 |
| *L. johnsonii* |  | 103786 |  |  | Fujisawa et al., 1992 |
| *L. johnsonii* | 33200 | 103620 | 9436 T |  | Fujisawa et al., 1992 |
| *L. johnsonii* | 332 | 103652 | 11468 |  | Fujisawa et al., 1992 |
| *L. johnsonii* | 11506 | 103653 | 9437 |  | Fujisawa et al., 1992 |
| *L. johnsonii* |  | 103654 |  |  | Fujisawa et al., 1992 |
| *L. johnsonii* |  | 103781 |  |  | Fujisawa et al., 1992 |
| *L. johnsonii* |  | 103782 |  |  | Fujisawa et al., 1992 |
| *L. johnsonii* La1 |  |  |  | NCC533 | Pridmore et al. (2004) |
| *L. gasseri* |  | 11413 |  |  |  |
| *L. gasseri* | 29601 | 11414 |  | I-4884 |  |
| *L. acidophilus* N FM | 700396 |  |  |  |  |

(*) CIP: Collection de l'Institut Pasteur, France
LMG: Laboratorium voor Microbiologie, Gent University, Belgium
CNCM: Collection Nationale de Microorganismes, Institut Pasteur, France
ATCC: American Type Tissue Collection, USA Example 13: Heterologous Expression of LjLa1 BSH in *E. Coli*

To study the properties of the LjLa1 BSHs, we cloned the BSH genes into a pStaby vector (StabyExpress, Delphigenetics) in order to purify BSHs using His-Tag system. *E.coli* expressions cells (*E. coli* SE, Delphigenetics) were then transformed The recombinant BSH-47 protein was produced in *E. coli* SE cells and purified using a His-Tag system (Sephadex Ni-NTA column, GE Healthcare). The activity of recombinant BSH-47 was tested using taurodeoxycholic (0.3%) and glycodeoxycholic (0.3%) LB agar (Chae et al 2013). After 48 h of incubation at 37° C., we observed that the recombinant BSH-47 is taurospecific (FIG. 9). Furthermore, the effect of recombinant LjLa1 BSH-47 has been studied on *Giardia* trophozoites cultures, in the presence or not of bovine bile (0.06 g/L). The results show that recombinant BSH-47 (0.96 U, with "U" designing enzymatic units) exhibits an inhibiting effect, the level of this inhibiting effect is equivalent to the inhibiting effect of *C. perfringens* BSH (1U) (FIG. 10).

Example 14: Characterization of the Inhibitory Activity of LjLa1 BSH-47 and BSH-56 In Vitro The effects of recombinant LjLa1 BSH-47 and BSH-56 were studied on cultures of *G. lamblia* trophozoites in either presence or absence of bovine bile (0.06 g/L). Recombinant BSH-56 was produced according to the process described for the production of BSH-47, such as described in Example 13. Several BSH concentration were tested ranging from 0.0001 µg/ml to 10 µg/ml. Interestingly, both BSH-47 (FIG. 11A) and BSH-56 (FIG. 11B) exhibit strong inhibitory effects. These results are in agreement with those obtained with commercial *C. perfringens* BSH (Example 8) (FIG. 10). As expected, no inhibitory effect was observed without bovine bile.

Specific Activities

Previous experiments allowed us to determine the substrate specificity of newly purified BSH-47 and BSH-56 and their specific activities had been determined. BSH-47 is able to deconjugate taurospecific bile salts while BSH-56 is able to deconjugate both taurospecific and glycospecific bile salts.

TABLE 6

| | Specific activity (µmole of glycine/ 5 min at 37° C./ mg of protein) | Specific activity (µmole taurine/ 5 min at 37° C./ mg of protein) |
|---|---|---|
| *C. perfringens* BSH | 0.690 | 0.150 |
| BSH-47 | 0.066 | 0.717 |
| BSH-56 | 0.536 | 2.604 |

Example 15: In Vivo Effect of *L. gasseri* CNCM I-4884 Against *G. Lamblia*

*L. johnsonii* La1 and *L. gasseri* CNCM I-4884 strains (*L. gasseri* CNCM I-4884 is also designated as *L. gasseri* ATCC29601 in FIG. 8 and in Table 5) were daily administered by intragastric gavage ($5 \times 10^8$ CFU) to neonatal mice from day 5 to day 15 (day of sacrifice). Mice were challenged with trophozoites at day 10 by intragastric gavage ($1 \times 10^5$ trophozoites) and then were sacrificed at day 15. Preliminary experiments allow us to determine that there is a peak in the *Giardia* infection rate 5 days postinoculation (data not shown). The presence of living trophozoites in the small intestine is a marker of *Giardia* infection. Mice were divided into three groups with a minimum of 8 animals per group. We observed a significant reduction ($p<0.05$) in the parasite load in the small intestine in groups treated with *L. gasseri* CNCM I-4884 compared to control animals administered with PBS (FIG. 12A). Interestingly, *L. gasseri* CNCM I-4884 was more efficient in reducing the number of trophozoites than *L. johnsonii* La1. In agreement with these observations, the counting of cysts in the large intestine showed a significant reduction ($p<0.05$) in groups treated with *L. gasseri* CNCM I-4884 compared to controls, whereas no significant reduction was observed in the group treated with *L. johnsonii* La1 (FIG. 12B).

Example 16: In Vivo Effect of BSH-47 Against *G. Lamblia*

Solutions of recombinant BSH-47 solutions (1 µg/ml, 10 µg/ml and 100 µg/ml diluted in NaHCO3 16.4%) were thawed and daily administered by intragastric gavage to neonatal mice (dose were respectively 0.05 mµg 0.5 µg and 5 µg per mice) from day 10 to day 15 (day of sacrifice). Control animals received PBS instead of BSH. All groups treated with BSH-47 showed a reduction in trophozoites load in the small intestine compared with the control (FIG. 13). However, only the group treated with 100 µg/ml of BSH-47 displayed significant reduction in the parasite load.

BIBLIOGRAPHIC REFERENCES

Ali, S. A. & D. R. Hill (2003), *Giardia intestinalis. Curr Opin Infect Dis*, 16, 453-60.

Benyacoub, J., P. F. Perez, F. Rochat, K. Y. Saudan, G. Reuteler, N. Antille, M. Humen, G. L. De Antoni, C. Cavadini, S. Blum & E. J. Schiffrin (2005) *J Nutr*, 135, 1171-6.

Biagini, G. A., Park, J. H., Lloyd, D., & Edwards, M. R. (2001), 3359-3365.

Brassard D and Schiffrin E J., 1997. *Trends Food Sci. Technol.* 8:321-326.

Carnaby, S., Katelaris, P. H., Naeem, A., & Farthing, M. J. G. (1994). DNA Fingerprinting, 62(5).

Charneau S, Junqueira M, Costa C M, Pires D L, Fernandes E S, Bussacos A C, et al. Int J Mass Spectrom 2007; 268:265-76. Farthing, M. J. (1997) *J Pediatr Gastroenterol Nutr*, 24, 79-88.

Farthing et al., (1986), M J 1986 *J Antimicrob Chemother* 17:165-171.

Fujisawa et al. (1992) Taxonomic Study of the *Lactobacillus acidophilus* Group, with Recognition of *Lactobacillus gallinarum* sp. nov. and *Lactobacillus johnsonii* sp. nov. and Synonymy of with the Type Strain of *Lactobacillus amylovorus*, (July), 487-491. Gillin, F. D. (1987). *Giardia* The Role of Conjugated and Unconjugated in Killing by Human Milk, 83, 74-83.

Grill J P, Cayuela C, Antoine J M, & Schneider F (2000) *J Appl Microbiol* 89(4):553-563.

Halliday et al., (1995) Int. J. for Parasitology, vol. 25(9), pp 1089-1097.

Humen, M. A., G. L. De Antoni, J. Benyacoub, M. E. Costas, M. I. Cardozo, L. Kozubsky, K. Y. Saudan, A. Boenzli-Bruand, S. Blum, E. J. Schiffrin & P. F. Perez (2005) *Infect Immun*, 73, 1265-9.

Lauer and Kandler (1980) Journal O Zentralbl Bakteriol Hyg Abt I Orig 1, 75-78, 1980.

Mons, C., A. Dumetre, S. Gosselin, C. Galliot & L. Moulin (2009) *Water Res*, 43, 211-7.

Morrison, H. G., A. G. McArthur, F. D. Gillin, S. B. Aley, R. D. Adam, G. J. Olsen, A. A. Best, W. Z. Cande, F. Chen, M. J. Cipriano, B. J. Davids, S. C. Dawson, H. G. Elmendorf, A. B. Hehl, M. E. Holder, S. M. Huse, U. U. Kim, E. Lasek-Nesselquist, G. Manning, A. Nigam, J. E. Nixon, D. Palm, N. E. Passamaneck, A. Prabhu, C. I. Reich, D. S. Reiner, J. Samuelson, S. G. Svard & M. L. Sogin (2007) *Science*, 317, 1921-6.

Paget, T., Maroulis, S., Mitchell, A., Edwards, M. R., Jarroll, E. L., Lloyd, D., & Lloyd, D. (2004). Printed in Great Britain, 1231-1236. doi:10.1099/mic.0.26836-0

Perez, P. F., J. Minnaard, M. Rouvet, C. Knabenhans, D. Brassart, G. L. De Antoni & E. J. Schiffrin (2001) *Appl Environ Microbiol*, 67, 5037-42.

Pridmore, R. D., B. Berger, F. Desiere, D. Vilanova, C. Barretto, A. C. Pittet, M. C. Zwahlen, M. Rouvet, E. Altermann, R. Barrangou, B. Mollet, A. Mercenier, T. Klaenhammer, F. Arigoni & M. A. Schell (2004) *Proc Nad Acad Sci USA*, 101, 2512-7.

Queiroz, R. M., Charneau, S., Motta, F. N., Santana, J. M., Roepstorff, P., and Ricart, C. A. (2013) *J Proteome Res* 12, 3255-3263

Rabilloud, T (2009) Membrane Proteomics Methods in Molecular Biology Volume 528, 2009, pp 259-267

Rohrer, L., Winterhalter, K. H., Eckert, J., & Kohler, P. (1986). Killing of *Giardia lamblia* by Human Milk Is Mediated by Unsaturated Fatty Acids, 30(2). doi:10.1128/AAC.30.2.254. Updated Singer, S. M. & T. E. Nash (2000) *J Infect Dis*, 181, 1510-2.

Smith, C. A., E. J. Want, G. O'Maille, R. Abagyan & G. Siuzdak (2006) *Anal. Chem.*, 78, 779-87.

Sud, M., E. Fahy, D. Cotter, A. Brown, E. A. Dennis, C. K. Glass, A. H. Merrill, Jr., R. C. Murphy, C. R. Raetz, D. W. Russell & S. Subramaniam (2007) *Nucleic Acids Res.*, 35, D527-32.

Tancrede, C. (1992) *Eur J Clin Microbial Infect Dis*, 11, 1012-5.

Uperoft, P. & J. A. Uperoft (2001) *Clin Microbial Rev*, 14, 150-64.

The invention claimed is:

1. A method of reducing the development of giardiasis in a subject, comprising administering a composition exhibiting a bile-salt hydrolase activity to a subject;
   wherein said composition is chosen from:
   a composition comprising at least one bile-salt hydrolase (BSH) enzyme, wherein said BSH enzyme has an amino acid sequence at least 95% identical to SEQ ID NO: 6;
   a composition comprising a lactic acid bacterium able to secrete at least one BSH enzyme, wherein said BSH enzyme has an amino acid sequence at least 95% identical to SEQ ID NO: 6, and wherein said lactic acid bacterium is not Lactobacillus johnsonii La1, Lactobacillus acidophilus, Bifidobacterium bifidum or Bifidobacterium infantis; and
   a combination thereof;
   wherein said bile-salt hydrolase activity is determined by the detection of the presence of glycine or taurine liberated from conjugated bile salts, of cholic acid, of deoxycholic acid and/or of chenodeoxycholic acid.

2. The method according to claim 1, wherein said bile-salt hydrolase activity is associated with the presence of at least one bile-salt hydrolase (BSH) enzyme.

3. The method according to claim 1, wherein said administered composition comprises a lactic acid bacterium able to secrete a BSH, wherein said bacterium is selected from:
   Lactobacillus, but not Lactobacillus johnsonii La1 or Lactobacillus acidophilus; and
   Bifidobacterium, but not Bifidobacterium bifidum or Bifidobacterium infantis.

4. The method according to claim 3, wherein said lactic acid bacterium is a Lactobacillus chosen from the group consisting of:
   Lactobacillus johnsonii, but not Lactobacillus johnsonii La1;
   Lactobacillus gasseri; and
   Lactobacillus acidophilus, but not Lactobacillus acidophilus La10; and
   Lactobacillus reuteri.

5. The method according to claim 3, wherein said Lactobacillus is chosen from the group consisting of the bacterial strains:
   Lactobacillus johnsonii filed at CNCM, Institut Pasteur, Paris, France, under reference 1-4885, on Aug. 7, 2014; and
   Lactobacillus gasseri filed at CNCM, Institut Pasteur, Paris, France, under reference 1-4884, on Aug. 7, 2014.

6. The method according to claim 1, wherein the subject is a human being.

7. The method according to claim 1, wherein the subject is a pig or cow.

8. A method of reducing the development of giardiasis in a subject, comprising administering a composition exhibiting a bile-salt hydrolase activity to a subject;
   wherein said composition comprises a lactic acid bacterium able to secrete at least one BSH enzyme, and wherein said lactic acid bacterium is not Lactobacillus johnsonii La 1, Lactobacillus acidophilus, Bifidobacterium bifidum or Bifidobacterium infantis;
   wherein said bile-salt hydrolase activity is determined by the detection of the presence of glycine or taurine liberated from conjugated bile salts, of cholic acid, of deoxycholic acid and/or of chenodeoxycholic acid.

9. The method according to claim 8, wherein said bile-salt hydrolase activity is associated with the presence of at least one bile-salt hydrolase (BSH) enzyme.

10. The method according to claim 9, wherein said BSH enzyme is a BSH from prokaryotes.

11. The method according to any claim 8, wherein said BSH enzyme comprises an amino acid sequence having at least 95% identity with an amino acid sequence chosen from the group consisting of: Lactobacillus johnsonii La1 BSH-12 (SEQ ID NO: 1), Lactobacillus johnsonii La1 BSH-47 (SEQ ID NO: 2), Lactobacillus johnsonii La1 BSH-56 (SEQ ID NO: 3), Lactobacillus gasseri BSH-A (SEQ ID NO: 4), Lactobacillus gasseri BSH-B (SEQ ID NO: 5), Lactobacillus johnsonii DPC 6026 BSH (SEQ ID NO: 6), Lactobacillus johnsonii DPC 6026 BSH (SEQ ID NO: 7), and Lactobacillus johnsonii DPC 6026 BSH (SEQ ID NO: 8).

12. The method according to claim 8, wherein said administered composition comprises a lactic acid bacterium able to secrete a BSH, wherein said bacterium is selected from:
   Lactobacillus, but not Lactobacillus johnsonii La1 or Lactobacillus acidophilus; and
   Bifidobacterium, but not Bifidobacterium bifidum or Bifidobacterium infantis.

13. The method according to claim 12, wherein said lactic acid bacterium is a Lactobacillus chosen from the group consisting of:
   Lactobacillus johnsonii, but not Lactobacillus johnsonii La1;
   Lactobacillus gasseri; and
   Lactobacillus acidophilus, but not Lactobacillus acidophilus La10; and
   Lactobacillus reuteri.

14. The method according to claim 12, wherein said Lactobacillus is chosen from the group consisting of the bacterial strains:
   Lactobacillus johnsonii filed at CNCM, Institut Pasteur, Paris, France, under reference 1-4885, on Aug. 7, 2014; and
   Lactobacillus gasseri filed at CNCM, Institut Pasteur, Paris, France, under reference 1-4884, on Aug. 7, 2014.

15. The method according to claim 8, wherein the subject is a human being.

16. The method according to claim 8, wherein the subject is a pig or cow.

17. A method of reducing the development of giardiasis in a subject, comprising administering a composition exhibiting a bile-salt hydrolase activity to a subject;
   wherein said composition:
   comprises a lactic acid bacterium able to secrete at least one BSH enzyme, wherein said BSH enzyme has an amino acid sequence at least 95% identical to SEQ ID NO: 6, and wherein said lactic acid bacterium is not Lactobacillus johnsonii La1, Lactobacillus acidophilus, Bifidobacterium bifidum or Bifidobacterium infantis;
   wherein said bile-salt hydrolase activity is determined by the detection of the presence of glycine or taurine liberated from conjugated bile salts, of cholic acid, of deoxycholic acid and/or of chenodeoxycholic acid.

18. The method according to claim 17, wherein said bile-salt hydrolase activity is associated with the presence of at least one bile-salt hydrolase (BSH) enzyme.

19. The method according to claim 17, wherein said administered composition comprises a lactic acid bacterium able to secrete a BSH, wherein said bacterium is selected from:
   Lactobacillus, but not Lactobacillus johnsonii La1 but not Lactobacillus acidophilus; and

*Bifidobacterium*, but not *Bifidobacterium bifidum* or *Bifidobacterium infantis*.

20. The method according to claim 19, wherein said lactic acid bacterium is a *Lactobacillus* chosen from the group consisting of:
*Lactobacillus johnsonii*, but not *Lactobacillus johnsonii* La1;
*Lactobacillus gasseri*; and
*Lactobacillus acidophilus*, but not *Lactobacillus acidophilus* La10; and
*Lactobacillus reuteri*.

21. The method according to claim 19, wherein said *Lactobacillus* is chosen from the group consisting of the bacterial strains:
*Lactobacillus johnsonii* filed at CNCM, Institut Pasteur, Paris, France, under reference 1-4885, on Aug. 7, 2014; and
*Lactobacillus gasseri* filed at CNCM, Institut Pasteur, Paris, France, under reference 1-4884, on Aug. 7, 2014.

22. The method according to claim 17, wherein the subject is a human being.

23. The method according to claim 17, wherein the subject is a pig or cow.

\* \* \* \* \*